US006730475B1

(12) United States Patent
Robertson et al.

(10) Patent No.: US 6,730,475 B1
(45) Date of Patent: May 4, 2004

(54) METHODS OF DIAGNOSIS AND TREATMENT OF MENIERE DISEASE

(75) Inventors: Nahid Robertson, Wellesley, MA (US); Cynthia Morton, Newton Centre, MA (US); Guy Van Camp, Antwerp (BE); Erik Fransen, Antwerp (BE); Paul Van de Heyning, Antwerp (BE)

(73) Assignees: Brigham and Women's Hospital, Boston, MA (US); University of Antwerp, Antwerp (BE)

( * ) Notice: Subject to any disclaimer, the term of this patent is extended or adjusted under 35 U.S.C. 154(b) by 0 days.

(21) Appl. No.: 09/579,288

(22) Filed: May 25, 2000

Related U.S. Application Data

(60) Provisional application No. 60/136,008, filed on May 26, 1999.

(51) Int. Cl.[7] .......... C12Q 1/68

(52) U.S. Cl. .......... 435/6; 435/69.1; 435/91.2; 514/44; 536/25.1; 536/25.5; 536/24.3

(58) Field of Search .......... 435/69.1, 91.2, 435/6; 514/44; 536/23.1, 23.5, 24.3

(56) References Cited

PUBLICATIONS

Agraves et al. (1987) *PNAS USA,* 84:464–468.
Bonaldo et al. (1989) *J. Biol. Ch em.,* 264:5575–5580.
Bonaldo et al. (1990) *Biochemistry,* 29:1245–1254.
Christiano et al. (1994) *J. Biol. Chem.,* 269:20256–20626.
Collins & Fuller (1968) *Science,* 162:1137–1139.
Colombatti et al. (1991) *Blood,* 77:2305–2315.
Colombatti et al. (1993) *Matrix,* 13:297–306.
deKok (1999) *Hum. Mol. Genet.* 8(2): 361–366.
deKok et al. (1995) *Science,* 267:685–688.
Duyk et al. (1992) *Nature Genet.,* 2:5–8.
Fishman et al. (1983) *Arch. Ophthalmal.,* 101:1367–1374.
Gerecke et al. (1997) *Genomics,* 41:236–242.
Halpin et al. (1998) *Am J. Audiol.,* 5:105–111.
Haudenschild et al. (1995) *J. Biol.,* 270:23150–23154.
Heller, et al. (1998) *Proc. Natl. Acad. Sci. USA,* 95: 11400–11405.
Iwanaga et al. (1992) *Thrombosis Res.,* 68:1.
Jenkins et al. (1990) *J. Biol. Chem.,* 265:19624–19631.
Kalafatis et al. (1987) *Blood,* 70:1577–1583.
Kelsell et al. (1997) *Nature,* 387:80–83.
Khetarpal et al. (1991) *Arch. Otolaryngol. Head & Neck Surg.,* 117:1032–1042.
Khetarpal et al. (1993) *Arch. Otolaryngol. Head & Neck Surg.,* 119:106–108.
Koller et al. (1989) *EMBO J.,* 8:1073–1077.
Liu et al. (1997) *Nature Genet.,* 16:188–190.
Mancuso et al. (1991) *Biochemistry,* 30:253–269.
Manolis et al. (1996) *Hum. Mol. Genet.,* 5:1047–1050.
Muta et al. (1991) *J. Biol. Chem.,* 266:6554.
Nakamura et al. (1998) *Eur. J. Biochem.,* 176:89.
Parente et al. (1991) *PNAS USA,* 88:6931–6935.
Pareti et al. (1987) *J. Biol. Chem.,* 262:13835–13847.
Petit et al. (1996) *Nature Genet.,* 14:385–391.
Robertson (1997) *Genomics* 46(3):345–354.
Robertson (1998) *Nature Genetics* 20(3): 299–303.
Robertson et al. (1994) *Genomics,* 23:42–50.
Roth et al. (1986) *Biochemistry,* 25:8357–8361.
Steel et al. (1994) *Trends in Genet.,* 10:428–434.
van Camp et al. (1997) *Am. J. Human Genet.,* 60:758–764.
Verhagen (1988) *Arch. Neurol.* 45:766–769.
Verhagen (1989) *J. Neurol. Sci.* 92:55–63.
Wälchi et al. (1993) *Eur. J. Biochem.,* 212:483–490.
Weil et al. (1997) *Nature Genet.,* 16:191–193.

*Primary Examiner*—Ulrike Winkler
(74) *Attorney, Agent, or Firm*—Fish & Richardson P.C.

(57) ABSTRACT

The invention features methods of diagnosing and treating Meniere disease. The invention also features kits and probes for diagnosing Meniere disease.

9 Claims, 9 Drawing Sheets

```
<400> 1
gcactcgggc gcagccgggt ggatctcgag caggtgtgag cagcctatca gtcacc atg       59
                                                              Met
                                                               1

tcc gca gcc tgg atc ccg gct ctc ggc ctc ggt gtg tgt ctg ctg ctg        107
Ser Ala Ala Trp Ile Pro Ala Leu Gly Leu Gly Val Cys Leu Leu Leu
            5                  10                  15

ctg ccg ggg ccc gcg ggc agc gag gga gcc gct ccc att gct atc aca        155
Leu Pro Gly Pro Ala Gly Ser Glu Gly Ala Ala Pro Ile Ala Ile Thr
        20                  25                  30

tgt ttt acc aga ggc ttg gac atc agg aaa gag aaa gca gat gtc ctc        203
Cys Phe Thr Arg Gly Leu Asp Ile Arg Lys Glu Lys Ala Asp Val Leu
    35                  40                  45

tgc cca ggg ggc tgc cct ctt gag gaa ttc tct gtg tat ggg aac ata        251
Cys Pro Gly Gly Cys Pro Leu Glu Glu Phe Ser Val Tyr Gly Asn Ile
50                  55                  60                  65

gta tat gct tct gta tcg agc ata tgt ggg gct gct gtc cac agg gga        299
Val Tyr Ala Ser Val Ser Ser Ile Cys Gly Ala Ala Val His Arg Gly
                70                  75                  80

gta atc agc aac tca ggg gga cct gta cga gtc tat agc cta cct ggt        347
Val Ile Ser Asn Ser Gly Gly Pro Val Arg Val Tyr Ser Leu Pro Gly
            85                  90                  95

cga gaa aac tat tcc tca gta gat gcc aat ggc atc cag tct caa atg        395
Arg Glu Asn Tyr Ser Ser Val Asp Ala Asn Gly Ile Gln Ser Gln Met
        100                 105                 110

ctt tct aga tgg tct gct tct ttc aca gta act aaa ggc aaa agt agt        443
Leu Ser Arg Trp Ser Ala Ser Phe Thr Val Thr Lys Gly Lys Ser Ser
    115                 120                 125

aca cag gag gcc aca gga caa gca gtg tcc aca gca cat cca cca aca        491
Thr Gln Glu Ala Thr Gly Gln Ala Val Ser Thr Ala His Pro Pro Thr
130                 135                 140                 145

ggt aaa cga cta aag aaa aca ccc gag aag aaa act ggc aat aaa gat        539
Gly Lys Arg Leu Lys Lys Thr Pro Glu Lys Lys Thr Gly Asn Lys Asp
                150                 155                 160

tgt aaa gca gac att gca ttt ctg att gat gga agc ttt aat att ggg        587
Cys Lys Ala Asp Ile Ala Phe Leu Ile Asp Gly Ser Phe Asn Ile Gly
            165                 170                 175

cag cgc cga ttt aat tta cag aag aat ttt gtt gga aaa gtg gct cta        635
Gln Arg Arg Phe Asn Leu Gln Lys Asn Phe Val Gly Lys Val Ala Leu
        180                 185                 190

atg ttg gga att gga aca gaa gga cca cat gtg ggc ctt gtt caa gcc        683
Met Leu Gly Ile Gly Thr Glu Gly Pro His Val Gly Leu Val Gln Ala
    195                 200                 205
```

FIG. 1

```
agt gaa cat ccc aaa ata gaa ttt tac ttg aaa aac ttt aca tca gcc      731
Ser Glu His Pro Lys Ile Glu Phe Tyr Leu Lys Asn Phe Thr Ser Ala
210                 215                 220                 225

aaa gat gtt ttg ttt gcc ata aag gaa gta ggt ttc aga ggg ggt aat      779
Lys Asp Val Leu Phe Ala Ile Lys Glu Val Gly Phe Arg Gly Gly Asn
                230                 235                 240

tcc aat aca gga aaa gcc ttg aag cat act gct cag aaa ttc ttc acg      827
Ser Asn Thr Gly Lys Ala Leu Lys His Thr Ala Gln Lys Phe Phe Thr
            245                 250                 255

gta gat gct gga gta aga aaa ggg atc ccc aaa gtg gtg gtg gta ttt      875
Val Asp Ala Gly Val Arg Lys Gly Ile Pro Lys Val Val Val Val Phe
        260                 265                 270

att gat ggt tgg cct tct gat gac atc gag gaa gca ggc att gtg gcc      923
Ile Asp Gly Trp Pro Ser Asp Asp Ile Glu Glu Ala Gly Ile Val Ala
    275                 280                 285

aga gag ttt ggt gtc aat gta ttt ata gtt tct gtg gcc aag cct atc      971
Arg Glu Phe Gly Val Asn Val Phe Ile Val Ser Val Ala Lys Pro Ile
290                 295                 300                 305

cct gaa gaa ctg ggg atg gtt cag gat gtc aca ttt gtt gac aag gct     1019
Pro Glu Glu Leu Gly Met Val Gln Asp Val Thr Phe Val Asp Lys Ala
                310                 315                 320

gtc tgt cgg aat aat ggc ttc ttc tct tac cac atg ccc aac tgg ttt     1067
Val Cys Arg Asn Asn Gly Phe Phe Ser Tyr His Met Pro Asn Trp Phe
            325                 330                 335

ggc acc aca aaa tac gta aag cct ctg gta cag aag ctg tgc act cat     1115
Gly Thr Thr Lys Tyr Val Lys Pro Leu Val Gln Lys Leu Cys Thr His
        340                 345                 350

gaa caa atg atg tgc agc aag acc tgt tat aac tca gtg aac att gcc     1163
Glu Gln Met Met Cys Ser Lys Thr Cys Tyr Asn Ser Val Asn Ile Ala
    355                 360                 365

ttt cta att gat ggc tcc agc agt gtt gga gat agc aat ttc cgc ctc     1211
Phe Leu Ile Asp Gly Ser Ser Ser Val Gly Asp Ser Asn Phe Arg Leu
370                 375                 380                 385

atg ctt gaa ttt gtt tcc aac ata gcc aag act ttt gaa atc tcg gac     1259
Met Leu Glu Phe Val Ser Asn Ile Ala Lys Thr Phe Glu Ile Ser Asp
                390                 395                 400

att ggt gcc aag ata gct gct gta cag ttt act tat gat cag cgc acg     1307
Ile Gly Ala Lys Ile Ala Ala Val Gln Phe Thr Tyr Asp Gln Arg Thr
            405                 410                 415

gag ttc agt ttc act gac tat agc acc aaa gag aat gtc cta gct gtc     1355
Glu Phe Ser Phe Thr Asp Tyr Ser Thr Lys Glu Asn Val Leu Ala Val
        420                 425                 430
```

FIG. 1A

```
atc aga aac atc cgc tat atg agt ggt gga aca gct act ggt gat gcc      1403
Ile Arg Asn Ile Arg Tyr Met Ser Gly Gly Thr Ala Thr Gly Asp Ala
    435                 440                 445

att tcc ttc act gtt aga aat gtg ttt ggc cct ata agg gag agc ccc      1451
Ile Ser Phe Thr Val Arg Asn Val Phe Gly Pro Ile Arg Glu Ser Pro
450                 455                 460                 465

aac aag aac ttc cta gta att gtc aca gat ggg cag tcc tat gat gat      1499
Asn Lys Asn Phe Leu Val Ile Val Thr Asp Gly Gln Ser Tyr Asp Asp
                470                 475                 480

gtc caa ggc cct gca gct gct gca cat gat gca gga atc act atc ttc      1547
Val Gln Gly Pro Ala Ala Ala Ala His Asp Ala Gly Ile Thr Ile Phe
            485                 490                 495

tct gtt ggt gtg gct tgg gca cct ctg gat gac ctg aaa gat atg gct      1595
Ser Val Gly Val Ala Trp Ala Pro Leu Asp Asp Leu Lys Asp Met Ala
        500                 505                 510

tct aaa ccg aag gag tct cat gct ttc ttc aca aga gag ttc aca gga      1643
Ser Lys Pro Lys Glu Ser His Ala Phe Phe Thr Arg Glu Phe Thr Gly
    515                 520                 525

tta gaa cca att gtt tct gat gtc atc aga ggc att tgt aga gat ttc      1691
Leu Glu Pro Ile Val Ser Asp Val Ile Arg Gly Ile Cys Arg Asp Phe
530                 535                 540                 545

tta gaa tcc cag caa taatggtaac attttgacaa ctgaaagaaa aagtacaagg     1746
Leu Glu Ser Gln Gln
                550

ggatccagtg tgtaaattgt attctcataa tactgaaatg ctttagcata ctagaatcag   1806
atacaaaact attaagtatg tcaacagcca tttaggcaaa taagcactcc tttaaagccg   1866
ctgccttctg gttacaattt acagtgtact ttgttaaaaa cactgctgag gcttcataat   1926
catggctctt agaaactcag gaaagaggag ataatgtgga ttaaaacctt aagagttcta   1986
accatgccta ctaaatgtac agatatgcaa attccatagc tcaataaaag aatctgatac   2046
ttagaccaaa agcaacattc gttctctaac cattctgtat tgattatata agcaaaatga   2106
aaagagaaac ttaaatgaac acagctcttt aacatggttc aggtacacat attttgaccc   2166
aagtggatat tttcttaaaa ccaatcaata atagctagct attactgcag actataaaat   2226
ctggatatag aaaggagacc tgtatcaaac tgcttttgta gtgtgttttc ataacaactt   2286
atgactaaaa atatcacact gaataagaga gcaggattgc caggtatttt tctatttctc   2346
tccttaattt tatatgtata tagatatatt tggcttatat tctaagtcac ctaagtactt   2406
aaaagttaag ttggtaaagt atttactgac tgcttataaa catttaaaga caaagacatt   2466
tcaaataact gcagaaaaaa tattgtagtt tgaatattta agcaataaaa ctgctagtga   2526
gttattgt                                                            2534
```

FIG. 1B

```
gcactcgggc gcagccgggt ggatctcgag caggtgtgag cagcctatca gtcacc atg    59
                                                              Met
                                                               1

tcc gca gcc tgg atc ccg gct ctc ggc ctc ggt gtg tgt ctg ctg ctg     107
Ser Ala Ala Trp Ile Pro Ala Leu Gly Leu Gly Val Cys Leu Leu Leu
            5                  10                  15

ctg ccg ggg ccc gcg ggc agc gag gga gcc gct ccc att gct atc aca     155
Leu Pro Gly Pro Ala Gly Ser Glu Gly Ala Ala Pro Ile Ala Ile Thr
        20                  25                  30

tgt ttt acc aga ggc ttg gac atc agg aaa gag aaa gca gat gtc ctc     203
Cys Phe Thr Arg Gly Leu Asp Ile Arg Lys Glu Lys Ala Asp Val Leu
    35                  40                  45

tgc tca ggg ggc tgc cct ctt gag gaa ttc tct gtg tat ggg aac ata     251
Cys Ser Gly Gly Cys Pro Leu Glu Glu Phe Ser Val Tyr Gly Asn Ile
50                  55                  60                  65

gta tat gct tct gta tcg agc ata tgt ggg gct gct gtc cac agg gga     299
Val Tyr Ala Ser Val Ser Ser Ile Cys Gly Ala Ala Val His Arg Gly
                70                  75                  80

gta atc agc aac tca ggg gga cct gta cga gtc tat agc cta cct ggt     347
Val Ile Ser Asn Ser Gly Gly Pro Val Arg Val Tyr Ser Leu Pro Gly
            85                  90                  95
cga gaa aac tat tcc tca gta gat gcc aat ggc atc cag tct caa atg     395
Arg Glu Asn Tyr Ser Ser Val Asp Ala Asn Gly Ile Gln Ser Gln Met
        100                 105                 110

ctt tct aga tgg tct gct tct ttc aca gta act aaa ggc aaa agt agt     443
Leu Ser Arg Trp Ser Ala Ser Phe Thr Val Thr Lys Gly Lys Ser Ser
    115                 120                 125

aca cag gag gcc aca gga caa gca gtg tcc aca gca cat cca cca aca     491
Thr Gln Glu Ala Thr Gly Gln Ala Val Ser Thr Ala His Pro Pro Thr
130                 135                 140                 145

ggt aaa cga cta aag aaa aca ccc gag aag aaa act ggc aat aaa gat     539
Gly Lys Arg Leu Lys Lys Thr Pro Glu Lys Lys Thr Gly Asn Lys Asp
                150                 155                 160

tgt aaa gca gac att gca ttt ctg att gat gga agc ttt aat att ggg     587
Cys Lys Ala Asp Ile Ala Phe Leu Ile Asp Gly Ser Phe Asn Ile Gly
            165                 170                 175

cag cgc cga ttt aat tta cag aag aat ttt gtt gga aaa gtg gct cta     635
Gln Arg Arg Phe Asn Leu Gln Lys Asn Phe Val Gly Lys Val Ala Leu
        180                 185                 190

atg ttg gga att gga aca gaa gga cca cat gtg ggc ctt gtt caa gcc     683
Met Leu Gly Ile Gly Thr Glu Gly Pro His Val Gly Leu Val Gln Ala
    195                 200                 205
```

FIG. 3

```
agt gaa cat ccc aaa ata gaa ttt tac ttg aaa aac ttt aca tca gcc      731
Ser Glu His Pro Lys Ile Glu Phe Tyr Leu Lys Asn Phe Thr Ser Ala
210                 215                 220                 225

aaa gat gtt ttg ttt gcc ata aag gaa gta ggt ttc aga ggg ggt aat      779
Lys Asp Val Leu Phe Ala Ile Lys Glu Val Gly Phe Arg Gly Gly Asn
                230                 235                 240

tcc aat aca gga aaa gcc ttg aag cat act gct cag aaa ttc ttc acg      827
Ser Asn Thr Gly Lys Ala Leu Lys His Thr Ala Gln Lys Phe Phe Thr
            245                 250                 255

gta gat gct gga gta aga aaa ggg atc ccc aaa gtg gtg gtg gta ttt      875
Val Asp Ala Gly Val Arg Lys Gly Ile Pro Lys Val Val Val Val Phe
        260                 265                 270

att gat ggt tgg cct tct gat gac atc gag gaa gca ggc att gtg gcc      923
Ile Asp Gly Trp Pro Ser Asp Asp Ile Glu Glu Ala Gly Ile Val Ala
    275                 280                 285

aga gag ttt ggt gtc aat gta ttt ata gtt tct gtg gcc aag cct atc      971
Arg Glu Phe Gly Val Asn Val Phe Ile Val Ser Val Ala Lys Pro Ile
290                 295                 300                 305

cct gaa gaa ctg ggg atg gtt cag gat gtc aca ttt gtt gac aag gct     1019
Pro Glu Glu Leu Gly Met Val Gln Asp Val Thr Phe Val Asp Lys Ala
                310                 315                 320

gtc tgt cgg aat aat ggc ttc ttc tct tac cac atg ccc aac tgg ttt     1067
Val Cys Arg Asn Asn Gly Phe Phe Ser Tyr His Met Pro Asn Trp Phe
            325                 330                 335

ggc acc aca aaa tac gta aag cct ctg gta cag aag ctg tgc act cat     1115
Gly Thr Thr Lys Tyr Val Lys Pro Leu Val Gln Lys Leu Cys Thr His
        340                 345                 350

gaa caa atg atg tgc agc aag acc tgt tat aac tca gtg aac att gcc     1163
Glu Gln Met Met Cys Ser Lys Thr Cys Tyr Asn Ser Val Asn Ile Ala
    355                 360                 365

ttt cta att gat ggc tcc agc agt gtt gga gat agc aat ttc cgc ctc     1211
Phe Leu Ile Asp Gly Ser Ser Ser Val Gly Asp Ser Asn Phe Arg Leu
370                 375                 380                 385

atg ctt gaa ttt gtt tcc aac ata gcc aag act ttt gaa atc tcg gac     1259
Met Leu Glu Phe Val Ser Asn Ile Ala Lys Thr Phe Glu Ile Ser Asp
                390                 395                 400

att ggt gcc aag ata gct gct gta cag ttt act tat gat cag cgc acg     1307
Ile Gly Ala Lys Ile Ala Ala Val Gln Phe Thr Tyr Asp Gln Arg Thr
            405                 410                 415

gag ttc agt ttc act gac tat agc acc aaa gag aat gtc cta gct gtc     1355
Glu Phe Ser Phe Thr Asp Tyr Ser Thr Lys Glu Asn Val Leu Ala Val
        420                 425                 430
```

FIG. 3A

```
atc aga aac atc cgc tat atg agt ggt gga aca gct act ggt gat gcc      1403
Ile Arg Asn Ile Arg Tyr Met Ser Gly Gly Thr Ala Thr Gly Asp Ala
    435                 440                 445

att tcc ttc act gtt aga aat gtg ttt ggc cct ata agg gag agc ccc      1451
Ile Ser Phe Thr Val Arg Asn Val Phe Gly Pro Ile Arg Glu Ser Pro
450                 455                 460                 465

aac aag aac ttc cta gta att gtc aca gat ggg cag tcc tat gat gat      1499
Asn Lys Asn Phe Leu Val Ile Val Thr Asp Gly Gln Ser Tyr Asp Asp
                470                 475                 480

gtc caa ggc cct gca gct gct gca cat gat gca gga atc act atc ttc      1547
Val Gln Gly Pro Ala Ala Ala Ala His Asp Ala Gly Ile Thr Ile Phe
            485                 490                 495

tct gtt ggt gtg gct tgg gca cct ctg gat gac ctg aaa gat atg gct      1595
Ser Val Gly Val Ala Trp Ala Pro Leu Asp Asp Leu Lys Asp Met Ala
        500                 505                 510

tct aaa ccg aag gag tct cat gct ttc ttc aca aga gag ttc aca gga      1643
Ser Lys Pro Lys Glu Ser His Ala Phe Phe Thr Arg Glu Phe Thr Gly
    515                 520                 525

tta gaa cca att gtt tct gat gtc atc aga ggc att tgt aga gat ttc      1691
Leu Glu Pro Ile Val Ser Asp Val Ile Arg Gly Ile Cys Arg Asp Phe
530                 535                 540                 545

tta gaa tcc cag caa taa tggtaacatt ttgacaactg aaagaaaaag             1739
Leu Glu Ser Gln Gln  *
                550

tacaagggga tccagtgtgt aaattgtatt ctcataatac tgaaatgctt tagcatacta   1799
gaatcagata caaaactatt aagtatgtca acagccattt aggcaaataa gcactccttt   1859

aaagccgctg ccttctggtt acaatttaca gtgtactttg ttaaaaacac tgctgaggct   1919
tcataatcat ggctcttaga aactcaggaa agaggagata atgtggatta aaaccttaag   1979
agttctaacc atgcctacta aatgtacaga tatgcaaatt ccatagctca ataaaagaat   2039
ctgatactta gaccaaaagc aacattcgtt ctctaaccat tctgtattga ttatataagc   2099
aaaatgaaaa gagaaactta aatgaacaca gctctttaac atggttcagg tacacatatt   2159
ttgacccaag tggatatttt cttaaaacca atcaataata gctagctatt actgcagact   2219
ataaaatctg gatatagaaa ggagacctgt atcaaactgc ttttgtagtg tgttttcata   2279
acaacttatg actaaaaata tcacactgaa taagagagca ggattgccag gtatttttct   2339
atttctctcc ttaattttat atgtatatag atatatttgg cttatattct aagtcaccta   2399
agtacttaaa agttaagttg gtaaagtatt tactgactgc ttataaacat ttaaagacaa   2459
agacatttca aataactgca gaaaaaatat tgtagtttga atatttaagc aataaaactg   2519
ctagtgagtt attgt                                                    2534
```

FIG. 3B

METHODS OF DIAGNOSIS AND TREATMENT OF MENIERE DISEASE

This application claims the benefit of a previously filed Provisional Application No. 60/136,008, filed May 26, 1999, the contents of which is incorporated in its entirety.

BACKGROUND OF THE INVENTION

Hearing loss is a heterogeneous disorder that affects over 14 million people in the United States, with approximately 1 of every 1000 infants being affected by congenital deafness. An estimated one-half of congenital hearing loss cases are due to genetic causes (Bieber and Nance (1979) *Clinical Genetics—A Sourcebook for Physicians*, Jackson and Schimke, eds., Wiley, N.Y., vol. 60, pp. 443–461). More than 175 different forms of hereditary deafness have been characterized, including autosomal dominant, autosomal recessive, X-linked, and mitochondrial forms (McKusick (1994) *Mendelian Inheritance in Man*, John Hopkins Univ. Press, Baltimore, Md.).

Genetic heterogeneity in hearing disorders both associated with other clinical anomalies (syndromic) and occurring as an isolated finding (nonsyndromic) indicates the involvement of a large number of genes in the complex development and function of the hearing process. Of the several hundred syndromic hearing loss disorders described (Gorlin et al. (1995) *Hereditary Hearing Loss and Its Syndromes*, Oxford Univ. Press, New York, N.Y.), only about 60 have been mapped to human chromosomes, with approximately half of these with characterized gene defects (Duyk et al., *Nature Genet*. 2:5–8, 1992; Petit, *Nature Genet*. 14:385–391, 1996). The majority of congenital hearing disorders are nonsyndromic (Cohen and Gorlin (1995) *Hereditary Hearing Loss and its Syndromes*, Gorlin, Toriello and Cohen, eds., Oxford Univ. Press, New York, N.Y., vol. 60, pp. 9–21), but even fewer nonsyndromic disorders have been identified. This number is increasing through the study of consanguineous geographically isolated families. Over 40 human chromosomal loci associated with nonsyndromic hearing impairment have been identified, some with corresponding mouse mutants in the homologous region (Petit (1996), supra; Van Camp et al., *Am. J Hum. Genet*. 60:758–764, 1997). However, to date, only a small number of nuclear genes responsible for nonsyndromic hearing impairment have been discovered. These include POU3F4 in DFN3 (de Kok et al. *Science* 267:685–688, 1995); MYO7A in DFNB2 (Liu et al., *Nature Genet*. 16:188–190, 1997; Weil et al. *Nature Genet*. 16:191–193, 1997) and DFN11 (Liu et al., *Nature Genet*. 17:268, 1997); POU4F3 in DFNA15 (Vahava et al., Science 279:1950, 1998); PDS in DFNB4 (Li et al.,*Nature Genet*18:215, 1998); TECTA in both DFNA8 and DFNA11 (Verhoeven et al., *Nature Genet*. 19:60, 1998); GJB2 in DFNB1 and DFNA3 (Kelsell et al., *Nature* 387:80–83, 1997).

The cause of many hearing disorders are still unknown. One such disorder is Meniere disease. Meniere disease is a syndrome in which hearing loss and imbalance problems co-occur. It is clinically characterized by recurrent episodes of vertigo associated with hearing loss and tinnitus with or without aural. Meniere disease is thought to be a multifactorial condition involving both genetic and environmental components.

SUMMARY OF THE INVENTION

The invention is based, at least in part, on the discovery that a nucleic acid and corresponding protein molecule (referred to herein as "COCH" or "COCH5B2") are associated with the hearing disorder, Meniere disease. It was found that a missense mutation in the wild-type COCH5B2 gene, leads to an amino acid substitution in the COCH5B2 protein and plays a role in Meniere disease. Thus, mutated COCH5B2 molecules (also referred to as mtCOCH5B2 molecules) as described herein are useful in diagnosing hearing disorders such as Meniere disease. In addition, wild-type COCH5B2 (referred herein as "COCH" or "COCH5B2") may be useful for the treatment of hearing disorders resulting from the expression and production of mtCOCH5B2. The properties of COCH5B2 are described in U.S. Ser. No. 09/394,264, which is incorporated herein by reference.

In general, the invention features a method of treating a subject at risk for (e.g., having or predisposed to) having Meniere disease. The method can include identifying an individual at risk for Meniere disease, and administering to the subject an effective amount of any of: COCH5B2 or a nucleic acid encoding it; an active fragment of COCH5B2 or a nucleic acid encoding it; an agonist of COCH5B2, e.g., a peptide or a peptomimetic analog; an antibody; or a small molecule, such that treatment of the subject occurs. Identification of an individual at risk for Meniere disease can be done in a number of different ways including: analyzing the family history of an individual; identifying an individual with vestibular dysfunction; identifying an individual by performing physical tests, e.g., otoscopy and pure tone audiometry; identifying an individual with a lesion in the COCH5B2 gene or mRNA; and/or identifying an individual with a mutant COCH5B2 protein sequence.

In a preferred embodiment, a method for treating a subject having Meniere disease comprises administering to the subject a COCH5B2 protein (SEQ ID NO:2), or portion thereof, such that treatment occurs. In another embodiment, Meniere disease can be treated by administering to the subject a nucleic acid encoding a COCH5B2 protein (SEQ ID NO:1 or SEQ ID NO3), or an active portion thereof, such that treatment occurs. The COCH5B2 molecule can be administered to a subject by any standard method, e.g., the COCH5B2 molecule can be administered by any of a number of different routes, e.g., intravenous, intradermal, subcutaneous, oral, transdermal (topical), or transmucosal administration.

In another aspect, the invention features a method of identifying an individual at risk for Meniere disease. The method includes detecting in the subject a genetic lesion(s) characterized by a mutation in the gene encoding a COCH5B2 protein (mtCOCH5B2 protein). In one embodiment, the lesion occurs in the COCH5B2 gene and a mutant mtCOCH5B2 protein is encoded. In another preferred embodiment, the lesion can be a deletion, insertion or substitution involving one or more nucleotides of the COCH5B2 gene, e.g., the lesion is a deletion or a substitution of nucleotide 151 of SEQ ID NO:3, e.g., the lesion is a substitution of the cytosine at nucleotide 151 of SEQ ID NO:3 to a thymidine. In another preferred embodiment, the lesion is a substitution, insertion or deletion of nucleotide 151 of SEQ ID NO:3, or a nucleotide which is 1, 2, 3, 5, 10 or more base-pairs on either side of nucleotide 151 of SEQ ID NO:3.

In one embodiment, the method includes contacting a sample, e.g., a cell sample, with a nucleic acid probe. In a preferred embodiment, the nucleic acid probe is capable of selectively binding a COCH5B2 nucleic acid sequence which contains a lesion, e.g., the probe only binds a COCH5B2 gene sequence which has a deletion, insertion or substitution. In a preferred embodiment, the probe binds a COCH5B2 sequence which has a substitution at nucleotide 151 of SEQ ID NO:3, e.g., the probe hybridizes to a COCH5B2 gene sequence that has a cytosine to thymidine substitution at nucleotide 151 of SEQ ID NO:3, e.g., the probe includes all or a portion of the nucleic acid sequence of SEQ ID NO:6 or the probe has the sequence 5'-tcctctgctcagggggc-3' (SEQ ID NO:6).

In another embodiment, the method includes using a probe which can bind a mutant COCH5B2 protein which has a deletion, insertion or substitution at one or more amino acid residues. In a preferred embodiment, the probe can be a labeled probe or an antibody which is capable of selectively binding a mutant COCH5B2 protein. In another preferred embodiment, the labeled probe or antibody can selectively bind a COCH5B2 protein which has a substitution at amino acid residue 51 of SEQ ID NO:2, e.g., the proline at residue 51 of SEQ ID NO:2 is substituted with a serine; or the probe can selectively bind a mutant COCH5B2 protein which contains a deletion, insertion or substitution of 1, 2, 3, 4, 5 or more residues on either side of residue 51 of SEQ ID NO:2.

In a preferred embodiment, the method, as described above, can also be used in fetal or neonatal diagnosis.

Another aspect of the invention features a method for diagnosing a subject as having Meniere disease. The method includes contacting the subject or a sample (e.g., a cell or tissue sample, e.g., a biopsy sample) from the subject with an agent capable of selectively detecting a mutant form of the COCH5B2 protein. In a preferred embodiment, the agent is a labeled probe or an antibody that can bind a mutant COCH5B2 protein, e.g., the agent can bind a COCH5B2 protein which has a deletion, insertion or substitution in the COCH5B2 protein. In a preferred embodiment, the method uses a probe that selectively binds to a COCH5B2 protein which has a mutant residue at position 51 of SEQ ID NO:2, e.g., the proline at amino acid 51 of SEQ ID NO:2 is substituted for a serine.

In another embodiment, the method for diagnosing a subject as having MeniEre disease is based on detection of a genetic lesion in the COCH5B2 nucleic acid sequence. In a preferred embodiment, the method involves identifying an individual at risk for Meniere disease, contacting a sample (e.g., a cell or tissue sample, e.g., a biopsy sample) from the subject with an agent capable of detecting a mutation in the COCH5B2 gene sequence. In a preferred embodiment, the agent is a nucleic acid probe that can selectively bind a mutant COCH5B2 nucleic acid sequence, e.g., the probe can detect a mutation or deletion specific for Meniere disease, e.g., the probe can detect a mutation occurring at nucleotide 151 of SEQ ID NO:3, e.g., the mutation is a substitution of a cytosine at nucleotide 151 of SEQ ID NO:3 for a thymidine. In a preferred embodiment, the probe includes all or a portion of the nucleic acid sequence of SEQ ID NO:6 or the probe has the sequence 5'-tcctctgctcagggggc-3' (SEQ ID NO:6). The method can also include comparing the sample from a subject at risk for Meniere disease to a control sample and forming a diagnosis based on whether a mutation is present as compared to the control sample. Specific diagnostic tests are described in greater detail below.

Another aspect of the invention features a kit for diagnosing a subject at risk for Meniere disease. The kit includes agents which can be used to detect whether a nucleic acid sequence from a subject of interest has a lesion in a COCH5B2 nucleic acid sequence or contains a mutant COCH5B2 protein. In one embodiment, a kit includes a nucleic acid probe which binds a COCH5B2 nucleic acid sequence which contains a lesion but not the wild type COCH5B2 sequence. In a preferred embodiment, the probe can bind a COCH5B2 nucleic acid sequence which contains a lesion, e.g., a COCH5B2 gene sequence which has a deletion, insertion or substitution. In a preferred embodiment, the probe selectively binds a COCH5B2 sequence which has a substitution at nucleotide 151 of SEQ ID NO:3, e.g., the probe selectively binds a COCH5B2 nucleic acid sequence where the cytosine at nucleotide 151 of SEQ ID NO:3 has been replaced with a thymidine e.g., a probe which includes all or a portion of the nucleic acid sequence of SEQ ID NO:6 or the probe which has the sequence 5'-tcctctgctcagggggc-3' (SEQ ID NO:6). In another embodiment, the kit also includes a probe which selectively hybridizes to the wild-type COCH5B2 nucleic acid, e.g., the probe cannot bind a COCH5B2 containing a deletion, insertion or substitution. In a preferred embodiment, the probe cannot bind a COCH5B2 gene sequence which has a substitution at nucleotide 151 of SEQ ID NO:3 or a COCH5B2 sequence which has a deletion, insertion or substitution of 1, 2, 3, 5, 10 or more basepairs on either side of nucleotide 151 of SEQ ID NO:3. In still yet another embodiment, the kit also includes a probe that is capable of selectively binding a mutant COCH5B2 protein. The probe can be a labeled probe or an antibody that can selectively bind a COCH5B2 protein which has a substitution at amino acid residue 51 of SEQ ID NO:2, e.g., the proline at residue 51 of SEQ ID NO:2 is substituted with a serine; or the probe can selectively bind a mutant COCH5B2 protein which contains a deletion, insertion or substitution of 1, 2, 3, 4, 5 or more residues on either side of residue 51 of SEQ ID NO:2. In another embodiment, the kit also includes standards and controls, e.g., the kit includes both wild type and mutant COCH5B2 nucleic acids. In still yet another preferred embodiment, an instruction leaflet is enclosed which outlines how to use the components of the kit to diagnose an individual with Meniere disease.

Another aspect of the invention features an isolated nucleic acid molecule (e.g., cDNAs) comprising a nucleotide sequence encoding a mutant COCH5B2 protein or a biologically active portion thereof, as well as, nucleic acid fragments suitable as primers or hybridization probes for the detection of mutant COCH5B2-encoding nucleic acid (e.g., mRNA) and mutations thereof. In one embodiment, the isolated nucleic acid sequence includes the nucleotide sequence of SEQ ID NO:4, or the coding sequence or complement of these nucleotide sequences. In another preferred embodiment, the isolated nucleic acid sequence encodes the amino acid sequence of SEQ ID NO:5.

A preferred COCH5B2 nucleic acid sequence encodes a protein which possesses at least one of the mtCOCH5B2 activities described herein.

In another embodiment, the isolated nucleic acid molecule encodes a protein, or portion thereof, wherein the protein, or portion thereof, includes an amino acid sequence which is sufficiently homologous to an amino acid sequence of SEQ ID NO:5. Preferably, the protein, or a portion thereof, encoded by the nucleic acid molecule of the invention maintains the ability to play a disruptive role in inner ear biology, e.g., vestibular dysfunction, e.g., the protein or portion may cause hearing loss associated with one or more of the following symptoms: dizziness, balance problems, oscillopsia, vertigo, tinnitus, aural fullness, or nausea in an individual. For example, the protein can be involved in disrupting one or more of the following inner ear biology activities: 1) it can interact, e.g., bind, with components of the extracellular matrix (e.g., fibrillar collagen, e.g., COL1A2, COL3A1); 2) it can modulate cell/extracellular matrix interactions; 3) it can modulate cell-cell adhesions; 4) it can interact, e.g., bind, with glycoproteins and/or proteoglycans for clearing them; 5) it can provide scaffolding by interacting with other extracellular matrix components (e.g., fibrillar collagen, e.g., COL1A2, COL3A1); and 6) it can modulate an inner ear secretory pathway (e.g., it can modulate production of acidophilic deposits).

In another embodiment, the isolated nucleic acid molecule is at least 15 nucleotides in length and hybridizes under stringent conditions to a nucleic acid molecule comprising the nucleotide sequence of SEQ ID NO:4. More preferably, the isolated nucleic acid encodes a naturally-occurring mutant human COCH5B2. In a preferred embodiment, the isolated nucleic acid is at least 5, 10, 15, 20, 25, 30, 35, 40, 50, 60, 100, 150, 200 nucleotides in length. For example, the probe can include all or a portion of the nucleic acid sequence of SEQ ID NO:6 or the probe can have the sequence 5'-tcctctgctcagggggc-3' (SEQ ID NO:6).

Other features and advantages of the invention will be apparent from the following detailed description and claims.

As used herein, the term "subject" refers to a mammal. Examples of mammals include human and non-human primates (e.g., a monkey), goats, pigs, cows, and rodents (e.g., a rat or a mouse) having a disorder associated with inner ear biology dysfunction, e.g., MeniEre disease. The mammal is preferably a primate, e.g., a human.

A "therapeutically effective amount" refers to an amount which is capable of, at least partially, reducing, alleviating or preventing Meniere disease. A therapeutically effective amount can be determined on an individual basis and is based, at least in part, on consideration of the species of mammal, the mammal's size, the agent used, the type of delivery system used, the time of administration relative to the severity of the disease, and whether a single, multiple, or a controlled release dose regimen is employed. A therapeutically effective amount can be determined by one of ordinary skill in the art employing such factors and using no more than routine experimentation.

BRIEF DESCRIPTION OF THE DRAWINGS

FIG. 1 depicts the cDNA sequence and predicted amino acid sequence of human COCH5B2. The nucleotide sequence corresponds to nucleic acids 1 to 2534 of SEQ ID NO:1. The amino acid sequence corresponds to amino acids 1 to 550 of SEQ ID NO:2.

FIG. 3 depicts the cDNA sequence and predicted amino acid sequence of mutant human COCH5B2 (mtCOCH5B2) as seen in subjects having Meniere disease. The nucleotide sequence corresponds to nucleic acids 1 to 2534 of SEQ ID NO:4. The amino acid sequence corresponds to amino acids 1 to 550 of SEQ ID NO:5.

DETAILED DESCRIPTION OF THE INVENTION

Figure 2:
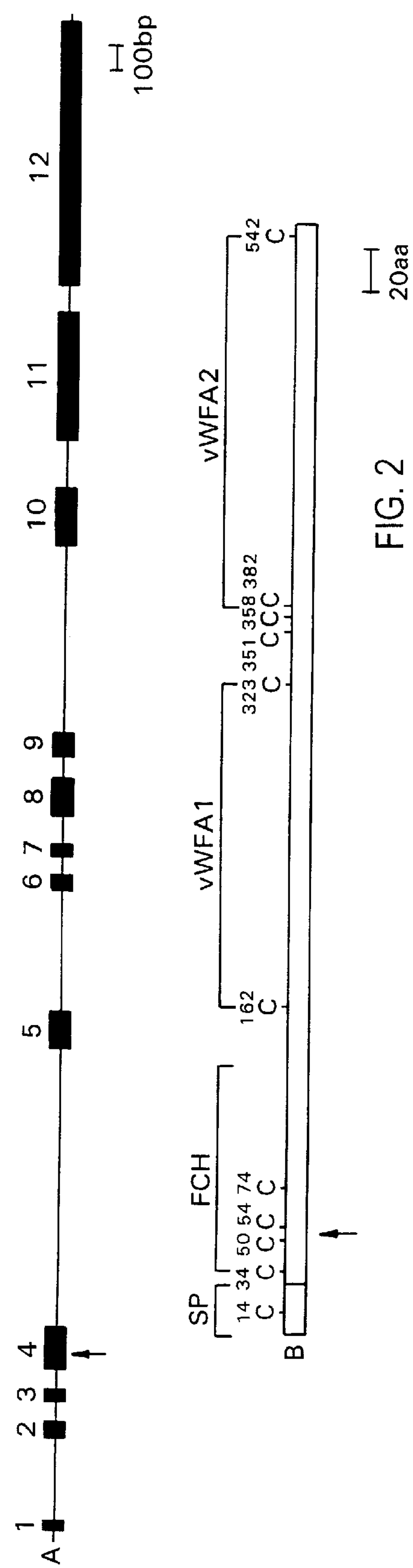
FIG. 2 is a schematic representation of genomic structure and the deduced amino acid sequence of COCH5B2. The schematic drawing of human COCH5B2 genomic structure shows intron-exon organization of the gene. Exons are indicated by shaded boxes. Position of the missense mutation found in Meniere disease is shown with an arrow. Introns of undetermined size are indicated ( ). The region of Limulus factor C homology (FCH) spans exons 4–6. The von Willebrand factor type A-like domain, vWFA1, is contained within exons 8–10; vWFA2 is in exons 11 and 12.

The invention is based, at least in part, on the discovery that the nucleic acid and corresponding protein molecule, referred to herein as COCH5B2, are associated with the hearing disorder Meniere disease. It was found that a missense mutation in the wild-type COCH5B2 gene, which results in an amino acid substitution in the COCH5B2 protein, plays a role in Meniere disease.

The COCH5B2 molecules have been associated with the modulation of an inner ear secretory pathway (Robertson et al. (1998) *Nat. Genetics* 20:299–303). Robertson et al. disclose that a mutant COCH5B2 protein is likely to be associated with the secretion of acidophilic mucosaccharide-containing ground substance. Histological examination of the inner ear of an individual with abherrant COCH5B2 gene sequence or COCH5B2 activity, e.g., DNAF9, showed conspicuous deposition of glycosaminoglycans in the spiral ligament, limbus, and the spiral lamina of the cochlea, as well as in the stroma of the maulae and cristea. These deposits obstruct the channels that accommodate the dentritic nerve fibers to the auditory and vesicular sense organs. The neuronal cell count was moderately reduced in the cochlea and severely reduced in the vestibular system, most likely due to retrograde neuronal degeneration (Khetarpl et al., *Arch. Otolaryngol. Head Neck Surg.* 117:1032–1042, 1991; Khetarpal et al., *Arch. Otolaryngol. Head Neck Surg.* 119:106–108, 1993). The expression patterns of these acidophilic deposits in the temporal bones of DFNA9 patients were found to parallel the expression pattern of COCH5B2.

Individuals having Meniere disease were discovered to have a lesion in the COCH5B2 gene sequence, which results in a mutant COCH5B2 protein. Mutational analysis of these individuals demonstrated that these individuals have a cytosine to thymidine missense mutation at nucleotide 151 of SEQ ID NO:3 resulting in a proline to serine ("P51S") substitution. The P51S mutation has several characteristics which indicate that this mutation plays a role in Meniere disease. For example, the following has been found about the P51S mutation: 1) no other variation was found in the COCH5B2 coding region in individuals having Meniere disease; 2) the P51S mutation was not found in the control population; and, 3) the P51S mutation lies adjacent to one of the conserved cysteine residues, which are likely to be involved in the structural integrity of the factor C homologous (FCH) domain of COCH5B2. Thus, the mutant serine at position 51 possibly interferes with proper COCH5B2 protein folding, its interaction with extracellular matrix proteins and/or it leads to the production of a deleterious substance. Accordingly, the COCH5B2 molecules and mutants thereof are useful in diagnosing a subject with Meniere disease.

The nucleotide sequence of the isolated mutant human COCH5B2 cDNA with the missense mutation at nucleotide 151 and the predicted amino acid sequence of the human mutant COCH5B2 protein are shown in FIG. 3 and in SEQ ID NOs:4 and 5, respectively.

Various aspects of the invention are described in further detail in the following subsections:

I. Isolated Nucleic Acid Molecules

One aspect of the invention features isolated nucleic acid molecules that encode a mutant COCH5B2 that are associated with the hearing disorder Meniere disease. The invention features nucleic acid molecules that encode mutant COCH5B2 ("mtCOCH5B2") or biologically active portions thereof, as well as, nucleic acid fragments sufficient for use as hybridization probes to identify a mutant COCH5B2-encoding nucleic acid (e.g., mtCOCH5B2 MRNA) and mutants thereof. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. An "isolated" nucleic acid molecule is a nucleic acid fragment which is separated from other nucleic acid molecules which are present in the natural source of the nucleic acid. Preferably, an "isolated" nucleic acid is free of sequences which naturally flank the nucleic acid (i.e., sequences located at the 5' or 3' ends of the nucleic acid) in the genomic DNA of the organism from which the nucleic acid is derived. For example, in various embodiments, the isolated mtCOCH5B2 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., an endothelial cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule for use in the present invention, e.g., a nucleic acid molecule having the nucleotide sequence of SEQ ID NO:4, or a portion thereof, can be isolated using standard molecular biology techniques and the sequence information provided herein. For example, a human COCH5B2 cDNA with a lesion can be isolated from a human cochlear library derived from an individual with Meniere disease using all or portion of SEQ ID NO:4 as a hybridization probe and standard hybridization techniques (e.g., as described in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989). Moreover, a nucleic acid molecule encompassing all or a portion of SEQ ID NO:4 can be isolated as described for the wild-type COCH5B2 protein, see U.S. Ser. No.: 09/394,264, the contents of which are incorporated herein by reference.

In a preferred embodiment, an isolated nucleic acid molecule for use in the invention includes the nucleotide sequence shown in SEQ ID NO: 1 or SEQ ID NO:4. The sequence of SEQ ID NO:1 corresponds to the wild-type human COCH5B2 cDNA, while the sequence of SEQ ID NO:4 corresponds to the mutated form of COCH5B2, mtCOCH5B2, which is found in subjects with Meniere disease. Preferably, the mtCOCH5B2 gene includes a cytosine to thymidine mutation at nucleotide 151 of SEQ ID NO:3. The mtCOCH5B2 cDNA includes sequences encoding the mtCOCH5B2 protein (i.e., "the coding region", from nucleotides 57–1709), as well as 5' untranslated sequences (nucleotides 1 to 56) and 3' untranslated sequences (nucleotides 1710–2534). Alternatively, the nucleic acid molecule can include only the coding region of SEQ ID NO:4 (e.g., nucleotides 57–1709).

In another preferred embodiment, an isolated nucleic acid molecule for use in the invention includes a nucleic acid molecule which is a complement of the nucleotide sequence shown in SEQ ID NO:1, SEQ ID NO:4 or a portion of either of these nucleotide sequences. A nucleic acid molecule which is complementary to the nucleotide sequence shown in SEQ ID NO:1 or SEQ ID NO:4 is one which is sufficiently complementary to the nucleotide sequence shown in SEQ ID NO:1 or SEQ ID NO:4 such that it can hybridize to the nucleotide sequence shown in SEQ ID NO:1 or SEQ ID NO:4, thereby forming a stable duplex.

Moreover, the nucleic acid molecule for use in the invention can include only a portion of the coding region of SEQ ID NO:1, or a portion of the coding region of SEQ ID NO:4, for example, a fragment which can be used as a probe or primer or a fragment encoding a biologically active portion of COCH5B2 or a mutant form of COCH5B2 (e.g., mtCOCH5B2). The nucleotide sequence determined from the cloning of the COCH5B2 gene from individuals with Meniere disease allows for the generation of probes and primers designed for use in identifying individuals with Meniere disease. The primers can also be used to clone missense mtCOCH5B2 homologues in other cell types, e.g. from other tissues, as well as mtCOCH5B2 homologues from other mammals. The probe/primer typically includes substantially purified oligonucleotide. The oligonucleotide typically includes a region of nucleotide sequence that hybridizes under stringent conditions to at least about 12, preferably about 25, more preferably about 40, 50 or 75 consecutive nucleotides of SEQ ID NO:4 sense or an anti-sense sequence of SEQ ID NO:4. Primers based on the nucleotide sequence in SEQ ID NO:4 can be used in PCR reactions to identify if an individual has a missense mutation. Probes based on the COCH5B2 nucleotide sequences can be used to detect transcripts or genomic sequences encoding the mtCOCH5B2 protein. In preferred embodiments, the probe further includes a label group attached thereto, e.g. the label group can be a radioisotope, a fluorescent compound, an enzyme, or an enzyme co-factor. Such probes can be used as a part of a diagnostic test kit for: identifying cells or tissue which express a mtCOCH5B2 protein, detecting the levels of missense COCH5B2 MRNA or determining whether a genomic COCH5B2 gene is mutated or deleted. For example, probes can also be used in diagnostic screening to identify individuals suffering from a hearing disorder, e.g., Meniere disease.

In one embodiment, the nucleic acid molecule of the invention encodes a protein or portion thereof which includes an amino acid sequence which is sufficiently homologous to an amino acid sequence of SEQ ID NO:5 such that the protein or portion thereof maintains one or more mtCOCH5B2 activities, e.g., are involved in disrupting inner ear biology activities. MtCOCH5B2 activities include: 1) disrupting the interaction, e.g., the binding, of components of extracellular matrix (e.g., fibrillar collagen, e.g., COL1A2, COL3A1); 2) disrupting cell/extracellular matrix interactions; 3) disrupting cell-cell adhesions; 4) disrupting the interaction, e.g., the binding, with glycoproteins and/or proteoglycans for clearing them; 5) disrupting the scaffolding by interacting with other extracellular matrix components (e.g., fibrillar collagen, e.g., COL1A2, COL3A1); 6) disrupting an inner ear secretory pathway (e.g., modulating production of acidophilic deposits); and is involved in Meniere disease. As used herein, the language "sufficiently homologous" refers to proteins or portions thereof which have amino acid sequences which include a minimum number of identical or equivalent (e.g., an amino acid residue which has a similar side chain as an amino acid residue in SEQ ID NO:4) amino acid residues to an amino acid sequence of SEQ ID NO:4, such that the protein or portion thereof is able to maintain one or more mtCOCH5B2 activities, e.g., plays a role in Meniere disease. In another embodiment, the protein has at least about 60–70%, preferably at least about 80–85%, and more preferably at least about 86, 88, 90%, and most preferably at least about 90–95%96%, 97%, 98% or 99% sequence identity to the entire amino acid sequence of SEQ ID NO:4. Methods of determining the percent homology between two amino acid sequences are set forth in U.S. Ser. No.:09/394,264.

Portions of proteins encoded by the COCH5B2 nucleic acid molecule are preferably biologically active portions of the COCH5B2 protein which play a role in hearing disorders, e.g., Meniere disease. As used herein, the term "biologically active portion of COCH5B2" is intended to include a portion, e.g., a domain/motif, of COCH5B2. Examples of biologically active portions of COCH5B2 which can be used in the invention are set forth in U.S. Ser. No.:09/394,264.

In addition to the human mtCOCH5B2 nucleotide sequence shown in SEQ ID NO:4, it will be appreciated by those skilled in the art that DNA sequence polymorphisms that lead to changes in the amino acid sequences of mtCOCH5B2 may exist within a population (e.g., the human population). Such genetic polymorphism in the mtCOCH5B2 gene may exist among individuals within a population due to natural allelic variation. As used herein, the terms "gene" and "recombinant gene" refer to nucleic acid molecules comprising an open reading frame encoding a mtCOCH5B2 protein, preferably a mammalian mtCOCH5B2 protein. Such natural allelic variations can typically result in 1–5% variance in the nucleotide sequence of the mtCOCH5B2 gene. Any and all such nucleotide variations and resulting amino acid polymorphisms in mtCOCH5B2 that are the result of natural allelic variation and that do not alter the functional activity of mtCOCH5B2 are intended to be within the scope of the invention. Moreover, nucleic acid molecules encoding mtCOCH5B2 proteins from other species, and thus which have a nucleotide sequence which differs from the human sequence of SEQ ID NO:4, are intended to be within the scope of the invention. Nucleic acid molecules corresponding to natural allelic variants and nonhuman homologues of the human mtCOCH5B2 cDNA of the invention can be isolated based on their homology to the human mtCOCH5B2 nucleic acid disclosed herein using the human cDNA, or a portion thereof, as a hybridization probe according to standard hybridization techniques under stringent hybridization conditions. Accordingly, in another embodiment, an isolated nucleic acid molecule of the invention is at least 15 nucleotides in length and hybridizes under stringent conditions to the nucleic acid molecule comprising the nucleotide sequence of SEQ ID NO:1 or SEQ ID NO:4. In other embodiments, the nucleic acid is at least 30, 50, 100, 205, 210, 220, 230, 250, 300, 400, 500, or 600 nucleotides in length. As used herein, the term "hybridizes under stringent conditions" refers to conditions for hybridization and washing under which nucleotide sequences typically remain hybridized to each other ("selectively bound"). Preferably, the conditions are such that sequences which have at least about 60%, at least about 65%, more preferably at least about 70%, and even more preferably at least about 75% or more sequence identity to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred example of stringent hybridization conditions are hybridization in 6×sodium chloride/sodium citrate (SSC) at about 45° C., followed by one or more washes in 0.2×SSC, 0.1 % SDS at 50–65° C. Preferably, an isolated nucleic acid molecule of the invention that hybridizes under stringent conditions to the sequence of SEQ ID NO:4 corresponds to a nucleic acid sequence which contains a lesion and encodes a mutant protein that plays a role in Meniere disease. A "wild-type" nucleic acid molecule refers to a nucleic acid molecule that is the naturally-occurring, normal, non-mutated version of a gene.

In addition to the nucleic acid molecules encoding mtCOCH5B2 proteins described above, another aspect of the invention features isolated nucleic acid molecules which are antisense thereto. An "antisense" nucleic acid includes a nucleotide sequence which is complementary to a "sense" nucleic acid encoding a protein, e.g., complementary to the coding strand of a double-stranded cDNA molecule or complementary to an mRNA sequence. Given the coding strand sequences encoding a mutated COCH5B2 disclosed herein (e.g., SEQ ID NO:4), antisense nucleic acids of the invention can be designed according to the rules of Watson and Crick base pairing. The antisense nucleic acid molecule can be complementary to the entire coding region of mtCOCH5B2 MRNA, but more preferably is an oligonucleotide which is antisense to only a portion of the coding or noncoding region of COCH5B2 mRNA. For example, the antisense oligonucleotide can be complementary to the region surrounding the translation start site of mtCOCH5B2 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a mtCOCH5B2 protein to thereby inhibit expression of the protein, e.g., by inhibiting transcription and/or translation. Antisense nucleic acid molecules can be administered by standard techniques, e.g., by direct injection, by modifying the nucleic acid molecule to target a specific cell and then administering it systemically. In addition, the antisense nucleic acid can be, for example, an a-anomeric nucleic acid molecule or a ribozyme.

II. Recombinant Expression Vectors and Host Cells

Another aspect of the invention features vectors, preferably expression vectors, containing a nucleic acid encoding COCH5B2 or mtCOCH5B2 (or portions thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

COCH5B2 or mtCOCH5B2 proteins can be expressed in bacterial cells such as *E. coli*, insect cells, yeast or mammalian cells (such as Chinese hamster ovary cells (CHO) or COS cells). Other suitable host cells are known to those skilled in the art. Expression vectors, and methods of expressing the COC5H2B protein or mtCOCH5B2 protein are described in detail in U.S. Ser. No.:09/394,264, which is incorporated herein by reference.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to COCH5B2 MRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

The host cells of the invention can also be used to produce nonhuman transgenic animals. The nonhuman transgenic animals can be used in screening assays designed to identify agents or compounds, e.g., drugs, pharmaceuticals, etc., which are capable of ameliorating detrimental symptoms of selected disorders such as Meniere disease. Methods of generating COCH5B2 mutant animals (e.g., mouse COCH5B2 gene sequence is modified such that the gene sequence has a particular mutation) are set forth in U.S. Ser. No.:09/394,264.

III. Isolated COCH5B2/mtCOCH5B2 Proteins and Anti-COCH5B2/mtCOCH5B2 Antibodies

Another aspect of the invention features isolated COCH5B2 and mtCOCH5B2 proteins, and biologically active portions thereof, as well as peptide fragments suitable for use as immunogens to raise anti-COCH5B2 or mtCOCH5B2 antibodies. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of COCH5B2 protein in which the protein is separated from cellular components of the cells in which it is naturally or recombinantly produced In one embodiment, the mtCOCH5B2 protein or portion thereof includes an amino acid sequence which is sufficiently homologous to an amino acid sequence of SEQ ID NO:5 such that the protein or portion thereof maintains one or more COCH5B2 activities. The portion of the protein is preferably a biologically active portion as described herein. In another preferred embodiment, the mtCOCH5B2 differs from the COCH5B2, e.g., by having a serine instead of a proline at amino acid sequence 51 of SEQ ID NO:2 (as shown in SEQ ID NO:5). The preferred mtCOCH5B2 proteins of the present invention also preferably possess at least one of the mtCOCH5B2 activities described herein.

COCH5B2 proteins, both wild-type and mutant, are preferably produced by recombinant DNA techniques. For example, a nucleic acid molecule encoding the protein is cloned into an expression vector (as described in U.S. Ser. No.09/394,264), the expression vector is introduced into a host cell and the COCH5B2 protein is expressed in the host cell. The COCH5B2 protein can then be isolated from the cells by an appropriate purification scheme using standard protein purification techniques. Alternative to recombinant expression, a COCH5B2 protein, polypeptide, or peptide can be synthesized chemically using standard peptide synthesis techniques. Moreover, mtCOCH5B2 protein can be isolated from cells (e.g., cells of the inner ear of an individual with Meniere disease), for example using an anti-COCH5B2 or anti-mtCOCH5B2 antibody.

The invention also provides COCH5B2 and mtCOCH5B2 chimeric or fusion proteins. Preferably, a COCH5B2 or mtCOCH5B2 chimeric or fusion protein of the invention is produced by standard recombinant DNA techniques as described in U.S. Ser. No.:09/394,264.

An isolated COCH5B2 protein, an isolated mtCOCH5B2 protein, or portions or fragments thereof, can be used as an immunogen to generate antibodies that bind COCH5B2 or mtCOCH5B2 using standard techniques for polyclonal and monoclonal antibody preparation. The full-length COCH5B2 or mtCOCH5B2 proteins can be used or, alternatively, the invention provides antigenic peptide fragments of COCH5B2 or mtCOCH5B2 for use as immunogens. The antigenic peptide of COCH5B2 or mtCOCH5B2 includes at least 8 amino acid residues of the amino acid sequence shown in SEQ ID NO:2 or SEQ ID NO:4 and encompasses an epitope of COCH5B2 or mtCOCH5B2 such that an antibody raised against the peptide forms a specific immune complex with the COCH5B2 or mtCOCH5B2 protein. Preferably, the antigenic peptide includes at least 10 amino acid residues, more preferably at least 15 amino acid residues, even more preferably at least 20 amino acid residues, and most preferably at least 30 amino acid residues. Preferred epitopes encompassed by the antigenic peptide are regions of COCH5B2 or mtCOCH5B2 that are located on the surface of the protein, e.g., hydrophilic regions.

A COCH5B2 or mtCOCH5B2 immunogen is typically used to prepare antibodies by immunizing a suitable subject, (e.g., rabbit, goat, mouse or other mammal) with the immunogen. An appropriate immunogenic preparation can contain, for example, recombinantly expressed mtCOCH5B2 proteins, or a chemically synthesized mtCOCH5B2 peptide. The preparation can further include an adjuvant, such as Freund's complete or incomplete adjuvant, or similar immunostimulatory agent. Immunization of a suitable subject with an immunogenic COCH5B2 or mtCOCH5B2 preparation induces a polyclonal anti-COCH5B2 or anti-mtCOCH5B2 antibody response, respectively.

Accordingly, another aspect of the invention features anti-COCH5B2 or anti-mtCOCH5B2 antibodies. The term "antibody" as used herein refers to immunoglobulin molecules and immunologically active portions of immunoglobulin molecules, i.e., molecules that contain an antigen binding site which specifically binds (immunoreacts with) an antigen, such as COCH5B2 or mtCOCH5B2. Examples of immunologically active portions of immunoglobulin molecules include F(ab) and $F(ab')_2$ fragments which can be generated by treating the antibody with an enzyme such as pepsin. The invention provides polyclonal and monoclonal antibodies that bind COCH5B2 or mtCOCH5B2. The term "monoclonal antibody" or "monoclonal antibody composition", as used herein, refers to a population of antibody molecules that contain only one species of an antigen binding site capable of immunoreacting with a particular epitope of COCH5B2 or COCH. A monoclonal antibody composition thus typically displays a single binding affinity for a particular COCH5B2 protein with which it immunoreacts.

Additionally, the production of recombinant anti-COCH5B2 antibodies is set forth in U.S. Ser. No.: 09/394,264, which is incorporated herein by reference An anti-COCH5B2 antibody or anti-mtCOCH5B2 (e.g., monoclonal antibody) can be used to isolate wild type and mutant COCH5B2 proteins, respectively. Methods of isolating antibodies and assays for isolating COCH5B2 proteins are set forth in U.S. Ser. No.:09/394,264, which is incorporated herein by reference.

IV. Pharmaceutical Compositions

The COCH5B2 or mtCOCH5B2 nucleic acid molecules, proteins, modulators, and antibodies (also referred to herein as "active compounds") of the invention can be incorporated into pharmaceutical compositions suitable for administration to a subject, e.g., can be used to treat an individual with Meniere disease. Such compositions typically include the nucleic acid molecule, protein, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a COCH5B2 protein or anti-COCH5B2 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the other required ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. 5,328,470) or by stereotactic injection (see e.g., Chen et al., *PNAS* 91:3054–3057, 1994). The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, modulators, and antibodies described herein can be used in one or more of the following methods: diagnostic assays; and methods of treatment. Diagnostic assays of the invention can also be used in fetal or neonatal diagnosis. Administration of a COCH5B2 protein can be used to, for example, treat Meniere disease. The isolated COCH5B2 nucleic acid molecule can be used to express COCH5B2 protein (e.g., via a recombinant expression vector in a host cell or in gene therapy applications) and can be used to treat a disorder where mtCOCH5B2 protein is produced, e.g., Meniere disease. The isolated COCH5B2 or mtCOCH5B2 of the present invention can be used to detect COCH5B2 mRNA (e.g., in a biological sample) or a genetic lesion in a COCH5B2 gene, e.g., Meniere disease, as described further below. Moreover, the anti-mtCOCH5B2 antibodies of the invention can be used to detect and isolate mtCOCH5B2 protein.

a. Diagnostic Assays:

The invention further provides a method for detecting the presence of mtCOCH5B2 in a biological sample. The method involves contacting the biological sample with a compound or an agent capable of detecting mtCOCH5B2 protein or mRNA such that the presence of mtCOCH5B2 is detected in the biological sample. In another embodiment, the biological sample is contacted with a compound or agent capable of detecting a mutant COCH5B2 protein or mRNA such that the presence of a mutant in COCH5B2 is detected in the biological sample. A preferred agent for detecting COCH5B2 mRNA, or mutants thereof, is a labeled or labelable nucleic acid probe capable of hybridizing to mtCOCH5B2 mRNA. The nucleic acid probe can be, for example, the full-length mutant COCH5B2 cDNA of SEQ ID NO:4 or portions thereof, such as an oligonucleotide of at least 15, 30, 50, 100, 205, 210, 220, 250 or 500 nucleotides in length and sufficient to specifically hybridize under stringent conditions to a COCH5B2 mutant mRNA. A preferred agent for detecting mtCOCH5B2 protein is a labeled or labelable antibody capable of binding to mtCOCH5B2 protein. Antibodies can be polyclonal, or more preferably, monoclonal. An intact antibody, or a fragment thereof (e.g., Fab or $F(ab')_2$) can be used. The term "labeled or labelable", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect COCH5B2 mutant mRNA or protein, in a biological sample in vitro as well as in vivo. For example, in vitro techniques for detection of COCH5B2 mutant mRNA include Northern hybridizations and in situ hybridizations. In vitro techniques for detection of COCH5B2 protein or mutants thereof include enzyme linked immunosorbent assays (ELISAs), Western blots, immunoprecipitations and immunofluorescence. Alternatively, COCH5B2 protein or mutant thereof can be detected in vivo in a subject by introducing into the subject a labeled anti-COCH5B2 or mtCOCH5B2 antibody. For example, the antibody can be labeled with a radioactive marker whose presence and location in a subject can be detected by standard imaging techniques.

The invention also encompasses kits for detecting the presence of mtCOCH5B2 in a biological sample. For example, the kit can include a labeled or labelable compound or agent capable of detecting mtCOCH5B2 protein or mRNA in a biological sample; means for determining the amount of mtCOCH5B2 in the sample; and means for comparing the amount of mtCOCH5B2 in the sample with a standard. The compound or agent can be packaged in a suitable container. The kit can further include instructions for using the kit to detect mtCOCH5B2 MRNA or protein.

The invention also encompasses kits for diagnosing patients affected with a hearing disorder, e.g., Meniere disease. For example, the kit can include a probe or a primer, e.g., a labeled or labelable probe or primer, capable of detecting a genetic lesion, e.g., a point mutation, e.g., thymidine substitution of a cytosine at nucleotide 151 of SEQ ID NO:1. The probe can be packaged in a suitable container. The probe or the primer is preferably derived from the factor C homologous region of COCH5B2 which contains COCH5B2 exons 4 and 5 and is approximately 100 amino acids in length. The kit can also include reagents required for PCR amplification and/or DNA sequencing. The kit can further include instructions for using the kit to diagnose a hearing disorder, e.g., Meniere disease.

The methods of the invention can also be used to detect genetic lesions in a COCH5B2 gene, thereby determining if a subject with the lesioned gene is at risk for a disorder characterized by aberrant or abnormal COCH5B2 nucleic acid expression or COCH5B2 protein activity, e.g., hearing loss disorder, e.g., Meniere disease. In a preferred embodiment, the methods includes identifying a person at risk for a hearing loss disorder, e.g., Meniere disease, and detecting, in a sample, e.g. a DNA sample, from the subject, the presence or absence of a genetic lesion characterized by at least one of an alteration affecting the integrity of a gene encoding a COCH5B2 protein, or the misexpression of the COCH5B2 gene. For example, such genetic lesions can be detected by ascertaining the existence of at least one of: 1) a deletion of one or more nucleotides from a COCH5B2 gene; 2) an addition of one or more nucleotides to a COCH5B2 gene; 3) a substitution of one or more nucleotides of a COCH5B2 gene, e.g., a substitution of a thymidine for a cytosine in SEQ ID NO:1; 4) a chromosomal rearrangement of a COCH5B2 gene; 5) an alteration in the level of a messenger RNA transcript of a COCH5B2 gene; 6) aberrant modification of a COCH5B2 gene, such as of the methylation pattern of the genomic DNA; 7) the presence of a non-wild type splicing pattern of a messenger RNA transcript of a COCH5B2 gene; 8) a non-wild type level of a COCH5B2-protein; 9) allelic loss of a COCH5B2 gene; and 10) inappropriate post-translational modification of a COCH5B2-protein. As described herein, there are a large number of assay techniques known in the art which can be used for detecting lesions in a COCH5B2 gene.

In certain embodiments, detection of the lesion involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080, 1988; and Nakazawa et al., PNAS91:360–364, 1994), the latter of which can be particularly useful for detecting point mutations in the COCH5B2-gene (see Abravaya et al., *Nucleic Acids Res.* 23:675–682, 1995). This method can include the steps of collecting a sample of cells from a patient, isolating nucleic acid (e.g., genomic, mRNA or both) from the cells of the sample, contacting the nucleic acid sample with one or more primers which specifically hybridize to a COCH5B2 gene under conditions such that hybridization and amplification of the COCH5B2-gene (if present) occurs, and detecting the presence or absence of an amplification product, or detecting the size of the amplification product and comparing the length to a control sample.

In an alternative embodiment, mutations in a COCH5B2 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the COCH5B2 gene and detect mutations by comparing the sequence of the sample COCH5B2 with the corresponding wild-type (control) sequence. Examples of sequencing reactions include those based on techniques developed by Maxim and Gilbert (*PNAS* 74:560, 1977) or Sanger (*PNAS* 74:5463, 1977). A variety of automated sequencing procedures can be utilized when performing the diagnostic assays (*Biotechniques* 19:448, 1995), including sequencing by mass spectrometry (see, e.g., PCT International Publication No. WO 94/16101; Cohen et al., *Adv. Chromatogr.* 36:127–162, 1996; and Griffin et al., *Appl. Biochem. Biotechnol.* 38:147–159, 1993).

Other methods for detecting mutations in the COCH5B2 gene include methods in which protection from cleavage agents is used to detect mismatched bases in RNA/RNA or RNA/DNA duplexes (Myers et al., *Science* 230:1242, 1985); Cotton et al., *PNAS* 85:4397, 1988; Saleeba et al., *Meth. Enzymol.* 217:286–295, 1992), electrophoretic mobility of mutant and wild type nucleic acid is compared (Orita et al. *PNAS* 86:2766, 1989; Cotton, *Mutat Res* 285:125-144, 1993; and Hayashi, *Genet Anal Tech Appl* 9:73–79, 1992), and movement of mutant or wild-type fragments in polyacrylamide gels containing a gradient of denaturant is assayed using denaturing gradient gel electrophoresis (Myers et al, *Nature* 313:495, 1985). Examples of other techniques for detecting point mutations include, selective oligonucleotide hybridization, selective amplification, and selective primer extension.

Accordingly, mutation analysis of COCH5B2 was performed on families with Meniere disease. To look for mutations in all coding exons of COCH5B2 in Meniere disease patients, human genomic clones were isolated using cDNA probes. PCR primer pairs were designed in COCH5B2 introns and used to amplify exons and splice junctions from total genomic DNA from individuals from families with Meniere disease. Amplified products were sequenced directly. Heterozygosity was discovered in one different nucleotide in the families, with one wild type allele and one mutated allele in all members tested with hearing loss: C→T substitution at nucleotide position 151 in exon 4. Additional molecular diagnostic testing was performed to confirm the missense mutation, such as allele-specific oligonucleotide (ASO) hybridization was performed on amplified genomic DNA from family members and unrelated controls. There was complete concordance of the mutated oligonucleotide hybridization with hearing-impaired individuals and absence of hybridization in all control individuals. Restriction digest of amplified DNA of families with Meniere disease was also used to test for the missense mutation.

b. Methods of Treatment

Another aspect of the invention features a method for treating a subject, e.g., a human, having a disease or disorder characterized by the expression of a COCH5B2 nucleic acid which contains a lesion in the nucleic acid sequence and encodes a mutant/abnormal COCH5B2 protein, e.g., Meniere disease. The method can include the step of administering wild-type COCH5B2 or a biologically active portion thereof such that treatment occurs. Aberrant or abnormal COCH5B2 activity refers to a non-wild-type COCH5B2 activity or a non-wild-type level of COCH5B2 activity. As the COCH5B2 protein is involved in inner ear biology, aberrant or abnormal COCH5B2 activity or expression can interfere, e.g., with the normal inner ear secretary pathway, e.g., it interferes with the production of acidophilic deposits. An example of a disorder or disease characterized by or associated with abnormal or aberrant COCH5B2 activity or expression includes Meniere disease. Additional methods of the invention include methods for treating a subject having a disorder characterized by aberrant COCH5B2 activity or expression. These methods include administering to the subject a wild-type COCH5B2 or a nucleic acid encoding it; an active fragment of COCH5B2 or a nucleic acid encoding it; an agonist of COCH5B2, e.g., an antibody or a small molecule, such that treatment of the subject occurs. The terms "treating" or "treatment", as used herein, refer to reduction or alleviation of at least one adverse effect or symptom of a disease or disorder, e.g., a disease or disorder characterized by or associated with abnormal or aberrant COCH5B2 protein activity or COCH5B2 nucleic acid expression, e.g., reduction or alleviation of symptoms associated with Meniere disease.

Alternatively, to treat a disease or disorder characterized by (or associated with) aberrant or abnormal (non-wild-type/mutant) COCH5B2 nucleic acid expression and/or COCH5B2 protein activity by inhibiting mtCOCH5B2 protein activity. A mtCOCH5B2 inhibitor can be an anti-mtCOCH5B2 antibody or a small molecule or other drug, e.g., a small molecule or drug identified using the screening assays described in the U.S. Ser. No. 09/394,264, which inhibits mtCOCH5B2 protein activity. It is desirable to treat a disease or disorder characterized by (or associated with) aberrant or abnormal (non-wild-type) COCH5B2 nucleic acid expression and/or COCH5B2 protein activity, e.g., Meniere disease, by stimulating wild-type COCH5B2 protein activity.

In addition, a subject having a hearing disorder such as Meniere disease can be treated according to the present invention by administering to the subject a wild-type COCH5B2 protein or portion thereof, or a nucleic acid encoding a wild-type COCH5B2 protein or portion thereof, such that treatment occurs.

Other aspects of the invention feature methods for modulating a cell associated activity. These methods include contacting the cell with an agent (or a composition which includes an effective amount of an agent) which modulates mtCOCH5B2 activity or mtCOCH5B2 expression such that a cell associated activity is altered relative to a cell associated activity of the cell in the absence of the agent. As used herein, "a cell associated activity" refers to a normal or abnormal activity or function of a cell. Examples of cell associated activities include cell-cell adhesion or cell/extracellular matrix interaction. The term "altered" as used herein refers to a change, e.g., an increase or decrease of a cell associated activity. In one embodiment, the agent stimulates wild-type COCH5B2 protein activity or wild-type COCH5B2 nucleic acid expression. In another embodiment, the agent inhibits mtCOCH5B2 protein activity or mtCOCH5B2 nucleic acid expression. Examples of such inhibitory agents include an antisense mtCOCH5B2 nucleic acid molecule, an anti-mtCOCH5B2 antibody, and an agent which inhibits mtCOCH5B2 protein activity or mtCOCH5B2 nucleic acid expression and which is identified using the drug screening assays described in U.S. Ser. No:09/394,264, which is incorporated herein by reference.

A COCH5B2 nucleic acid molecule, a COCH5B2 protein, etc. used in the methods of treatment can be incorporated into an appropriate pharmaceutical composition described herein and administered to the subject through a route which allows the molecule, protein, modulator, etc. to perform its intended function. Examples of routes of administration are also described herein.

This invention is further illustrated by the following examples which should not be construed as limiting. The contents of all references, patent applications, patents, and published patent applications cited throughout this application are hereby incorporated by reference.

EXAMPLES

Materials and Methods

Family Pedigree of Individuals with Meniere Disease

Figure 4:
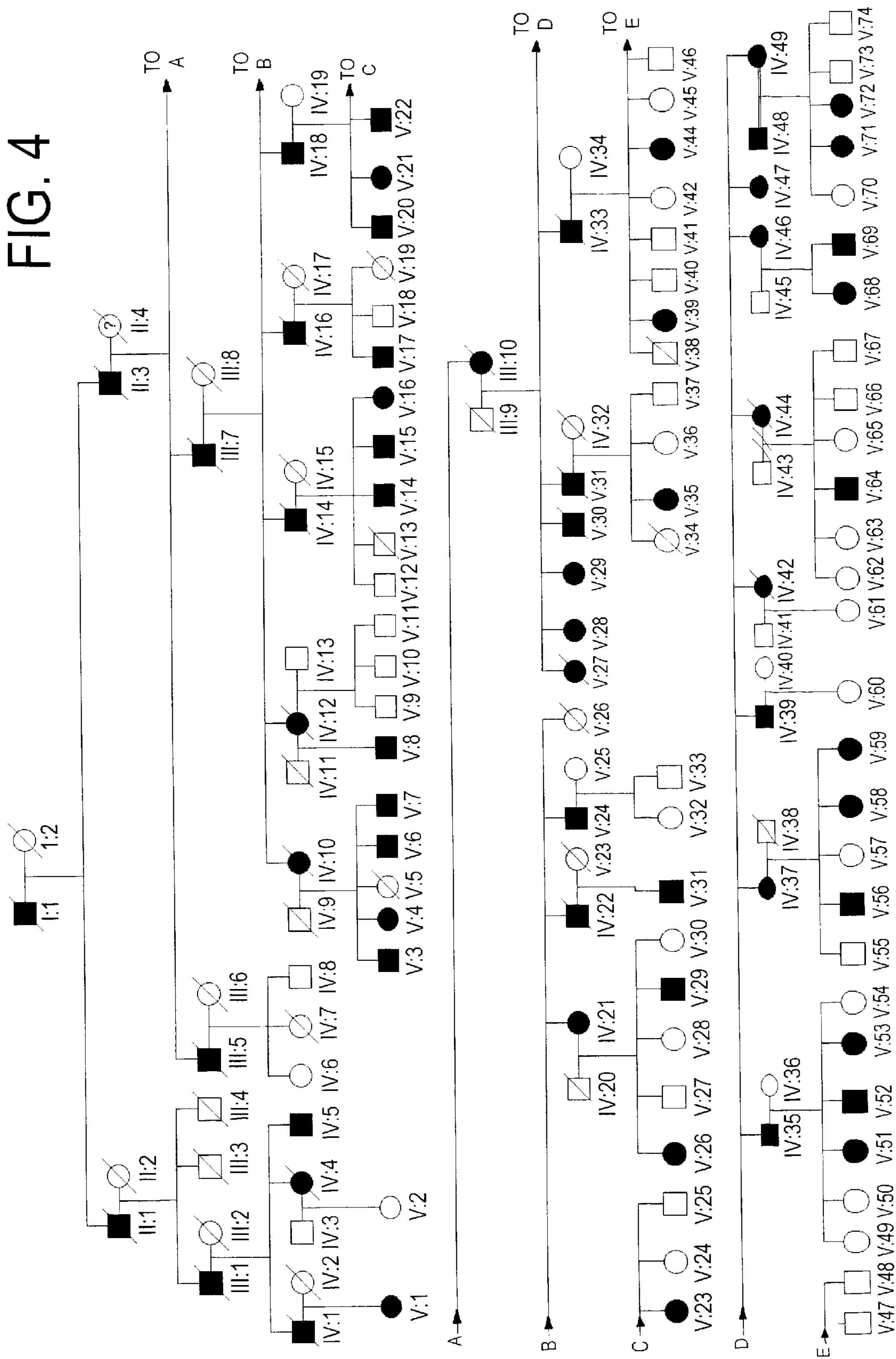
FIG. 4 depicts the entire pedigree of a large Belgian family which has members with Meniere disease. Open symbols indicate unaffected individuals; solid symbols indicate affected individuals; and individuals who are deceased are indicated by a slash. Family members who are heterozygous for the proline to serine ("P51S") mutation are indicated by a "+". One family member who is homozygous for this mutation is indicated by "++". The ages of the surviving family members are provided.
Figure 5:
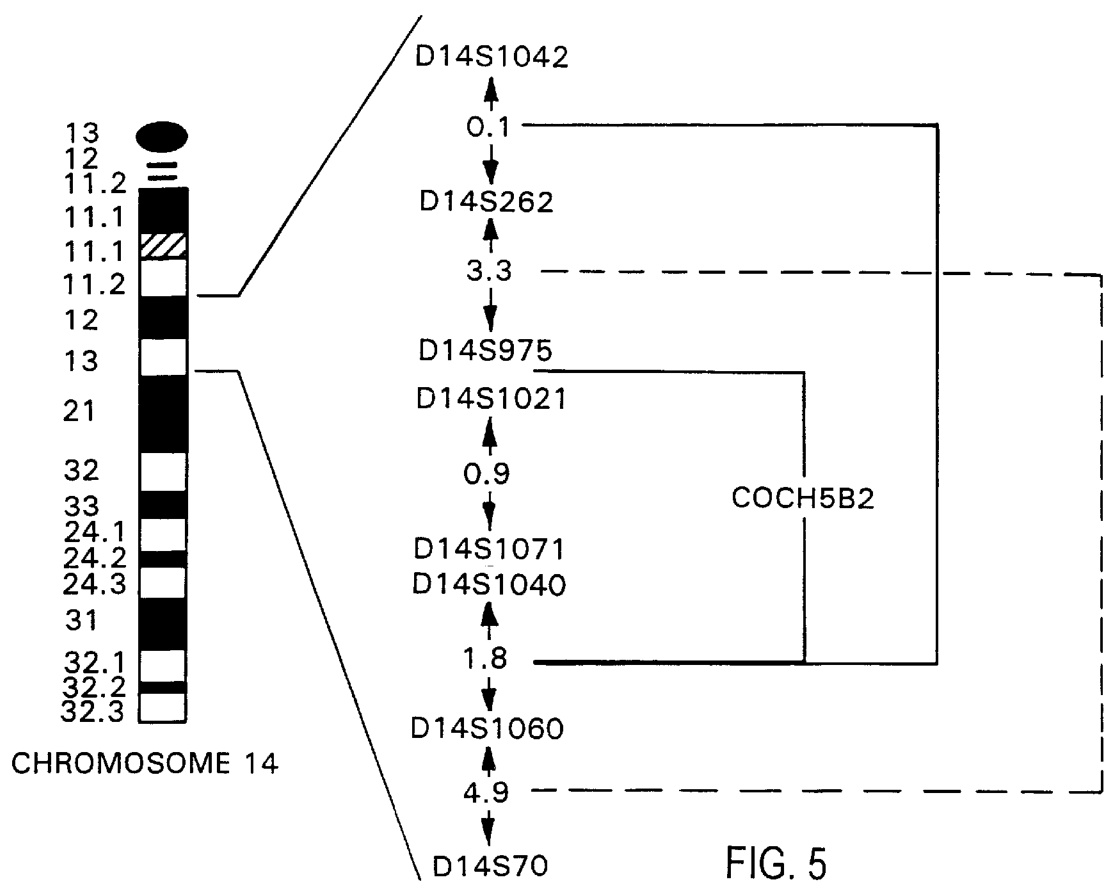
FIG. 5 depicts the DFNA9 candidate region. The ideogram of human chromosome 14 indicates the original 9 cM DFNA9 candidate region, as well as the region which the COCH5B2 transcript has been mapped. For the Belgian family having members with Meniere disease, the disease locus is mapped to a 6 cM interval between markers D14S1042 and D14S1071.

A family pedigree of the Belgian family with Meniere disease (also referred to as family 1) is shown in FIG. 4. The pedigree of family 1 consists of 5 generations. The inheritance pattern is autosomal dominant and fully penetrant. A blood sample was obtained from 119 family members after informed consent. The family originates from an area which has remained relatively isolated and rural until two generations ago.

The pedigree consists of a subset of the entire pedigree of family 1, comprising only family members from whom DNA was available. Of the family members who were not affected as indicated by the open symbols in FIG. 4, many are younger than the cutoff age (55) for Meniere disease.

One documented consanguineous marriage occurred between the individuals V-8 and IV-49. To simplify the pedigree, one individual is represented at 2 different places in the pedigree (Individual V-8 is the same person as individual IV-48 (FIG. 4). However, it is likely that other consanguineous marriages have occurred in the past. This is especially relevant when considering generation 3, which contains two affected siblings (III-7 and III-10) of whom all children (respectively 8 and 14) are affected. The ninth child of patient III-7, individual IV-26, died at the age of 7, which is well before the age of onset of the disease, and was therefore not taken into account. The most likely explanation for this observation is that individuals III-7 and III-10 were homozygous for the disease allele. In that case, both parents of sibs III-7 and 111-10 must have been affected. Unfortunately, it has not been possible to determine the affection status of individual 11-4 on an anamnestic basis.

Clinical Evaluation of Individuals with Meniere Disease

In family 1, clinical data with special relevance to hearing and imbalance complaints were collected from 120 family members using questionnaires and interviews. Otoscopy and pure tone audiometry were performed in a quiet, but not soundproof, room.

These analyses revealed a progressive perceptive hereditary hearing impairment typically starting between ages 40-55, and resulting in profound hearing loss. The vestibular symptoms start around the same age as the hearing loss. All of the patients reported instability in darkness. Most of them reported a tendency to fall sideways, as well as positional vertigo. More than one fourth of the patients reported vertigo attacks with accompanying hearing loss, tinnitus, aural fullness, nausea and vomiting. These episodes last for more than 24 hours in most cases. Besides cochleo-vestibular complaints, no other consistent clinical abnormalities were reported. In total, 35 family members were affected.

One of these patients, V-71, who was born from the consanguineous marriage between individuals V-8 and IV-49, had a markedly earlier age of onset.

In 23 affected family members, additional hearing tests and vestibular function analyses have been performed. The hearing tests included otoscopy, air and bone condition, pure tone audiometry in a soundproof room, speech audiometry, short increment sensitivity index test, tone decay test, impedance audiometry, brain stem evoked response audiometry, and otacoustic emissions. Vestibular function tests included electronystagmography (ENG) and on-line three-dimensional video-oculography (VOG). The ENG tests comprise an oculomotor test, spontaneous and positional nystagmus registration, rotary chair est (0.05 Hz) and bithermal caloric irrigation. The VOG test consists of ocular counter roll measurements during otolith stimulation elicited by movement of the patient's head in the roll plane (shoulder-to-shoulder). The combination of ENG and VOG assesses both semicircular and otolith function. The audiometric data revealed that persons younger than 45 years generally have mild hearing loss, with the high frequencies being more affected than the low frequencies. The persons older than 65 years are, in most cases, severely and profoundly affected across all frequencies. Persons between 45 and 65 years have moderate to severe hearing loss, with some patients having asymmetry between the two ears. This suggests that the period between age 45 and 65 marks a transition period, characterized by a progressive hearing loss, whereby a transient asymmetry sometimes occurs. Semicircular canal function, as assayed by the rotatory chair test and caloric irrigation, shows bilateral vestibular hypo or areflexia in the patient population. The VOG test indicated that the otolith organs are also affected. Here too, a progression pattern comparable to the hearing deterioration is observed. In the beginning which is at about age 45, the patients have normal and symmetric vestibular function. This is followed by a transition period between ages 46-55 whereby vestibular function deteriorated and asymmetry of the vestibule may occur. The progressive vestibular dysfunction eventually results in total vestibular areflexia, eliminating the asymmetry.

Family 2 was described by Verhagen et al. (1988) *Arch. Neurol*. 45:766–769. In brief, patients suffered from instability in the dark and a progressive hearing loss starting around the age of 40. None of the patients suffered from episodic vertigo.

Family 3 was described by Verhagen et al. (1989) J *Neurol. Sci*. 92:55–63. Here too, a progressive hearing loss and balance complaints started around the age of 40. All patients reported dizziness, and instability in the dark. Two out of five cases reported episodes of vertigo.

Linkage Analysis of Individuals with Meniere Disease

DNA was isolated from the blood using standard procedures. Polymorphic markers were analyzed radioactively. One primer was end-labeled with $^{32}P$, and a standard PCR reaction was performed on 50 ng of genomic DNA. PCR products were separated on a denaturing polyacrylamide gel, and the bands were visualized by autoradiography. Two-point LOD scores were calculated using the LINKAGE software package version 5.1. The gene frequency for hearing loss due to mutations in this gene was set at 0.0001. Recombination frequencies were assumed to be equal for males and females. The allele frequencies were assumed to be 1/n, with n being the number of observed alleles in the family. The disease was assumed to be fully penetrant, without phenocopies.

For linkage analysis, a subset of the pedigree was used which included 23 family members. Since DFNA 9 was the only locus for autosomal dominant non-syndromic hearing loss associate with vestibular pathology, it was analyzed first whether the disease in our family was linked to this locus. LOD scores above 4 were obtained for marker D14S262. Subsequently, haplotyping for the entire family (119 family members) was performed using markers D14S1060, D14S 1071, D14S262 and D14S 1021 (data not shown). The size of the candidate region was 6cM, with no recombination between markers D14S262 and D14S1071. One individual born from a consanguineous marriage (V-71), was homozygous for the disease haplotype.

Close linkage between the disease and markers surrounding the DFNA9 locus, on chromosome 14ql2–13, was found. Mutation analysis of the COCH-5B2 gene, which is responsible for DFNA9, revealed a missense point mutation in the exon 4 of this gene. Also, in two small families with similar vestibulo-cochlear symptoms, the same mutation was found. The mutation leads to the substitution of a Pro by a Ser at amino acid 51 of SEQ ID NO:2 (P5IS). The disease locus for the family reported here was mapped to a 6 cM interval between markers D14S1042 and D14S1071, overlapping with both the original candidate interval and with the COCH5B2 interval as shown in FIG. 7. Briefly, FIG. 7 is an ideogram of human chromosome 14, the markers of the original 9 cM DFNA9 candidate region (Manolis et al. (1996) *Human Mol. Genet*. 5:1047–1050) are indicated, as well as the region to which the COCH5B2 transcript had been mapped (Robertson (1997) *Genomics* 46:345–354).

Sequence and Restriction Analysis of Individuals with Meniere Disease

All coding errors of the COCH5B2 gene were amplified in a standard non-radioactive PCR reaction, using the primers and reaction conditions described previously (Robertson et al. (1998) *Nat. Genetics* 20:299–303). Briefly, 100 ng of genomic DNA was taken as a template and was amplified using primers flanking each coding exon of the COCH5B2 gene. PCR amplification was carried out in a thermal cycler through 35 cycles of 1 minute at 95° C., 1 minute at 55° C., 1 minute at 72° C. using Silverstar Taq DNA polymerase (Eurogentec, Seraing, Belgium).

PCR products were analyzed on an agarose gel, cut out of the gel and purified using the Sephaglass BandPrep kit (Pharmacia, Uppsala, Sweden). 10 ng of purified DNA was used in a cycle-sequencing reaction using the Dye Terminator Sequencing Ready Reaction kit (Perkin Elmer, Branchburg). Fragments were analyzed using a 377 ABI automated sequencer. In the fast assay for the P51S mutation, PCR product of exon 4 was digested with the restriction enzyme Bgl1 (Amersham) according to the manufacturer's instructions. Reaction products were analyzed on a 1% agarose gel and stained with ethidium bromide. In brief, the P51S mutation destroys a Bgl1 restriction site. The presence of the mutation can therefore be assayed by a PCR of exon 4, followed by Bgl1 digestion. In controls, the 295 bp PCR product was cleaved into two fragments of 157 and 138 bp, respectively. In case of the P5S mutation, the PCR product was not cleaved and the undigested 295 bp band is visible.

To investigate whether mutations in the COCH5B2 gene were responsible for the audiovestibular symptoms in family 1, mutation analysis was performed. All coding exons of COCH5B2, including the intro-exon boundaries, were sequenced in one affected individual who is homozygous for the disease haplotype, individual V-71, in two individuals who are heterozygous (IV-5 and IV-48) and in two controls. In exon 4, a cytosine to thymidine point mutation was found at base repair 151 of the coding region in the patients but not in the controls. The nucleotide numbering of COCH5B2 is based upon the sequence of SEQ ID NO:3, with first base of the AUG start codon being nucleotide 1. This mutation is expected to lead to the substitution of a proline residue by a serine in the amino acid residue 51 of the COCH5B2 protein (P51S) (SEQ ID NO:2). Haplotype analysis confirmed that individual V-71 was homozygous for the mutation, whereas the patients IV-5 and IV-48 were heterozygous. Just as the three previously described mutations, the P51S mutations occurs in the cysteine-rich domain of COCH5B2 termed the FCH (Factor C Homologous) domain. No other DNA variations leading to amino acid changes were found.

The P51S mutations destroy a site for the restriction enzyme Bgl 1. This provided a rapid screening assay for the P51S mutation. Analysis of the P51S mutation in all family members from whom DNA was also available, indicated that the segregation of the mutation in the pedigree was in agreement with the haplotype results. To analyze whether the P51S mutation was also responsible for the disease in two small Dutch families 2 and 3, two patients from family 2 and 3 members of family 3 were screened for the mutation using the same restriction assay. This revealed that the P51S mutation is also presented in these two families. To exclude that the P51S variation was a common polymorphism, 100 independent controls of Belgian origin were analyzed using this assay, but he mutation was never found.

Interestingly, one individual from a consanguineous marriage between two patients, is homozygous for the PSIS mutation. This person (V-71) differed from the other patients by the fact that the age of onset of the disease in this individual was around age 25, while, for the rest of the patients, which are heterozygous for the mutation, the age of onset usually lies within their forties. She was the youngest family member in which the disease could be clinically recognized. At the age of 34, the clinical picture was similar to what is typically observed in patients where the disease is in a final state.

The way in which the P51S mutation causes the disease can be any of the following: 1) the P51S mutation leads to a mere loss of function; 2) the mutation has a dominant-negative effect; and/or 3) the P51S mutation causes gain of function, whereby the mutant protein obtains deleterious novel properties. If the P51S mutation leads to a mere loss of function, then patients who are heterozygous for the mutation would show the disease phenotype due to a diminished abundance of COCH5B2 protein. Although a loss-of-function cannot be completely excluded, it does not seem very likely that the difference between a diminished abundance and the total absence of protein would just be reflected as a lower age of onset in the homozygous patient. If the P51S mutation has a dominant-negative effect, it is expected that the phenotype of the homozygote and the heterozygote be the same, since the protein would be non-functional in both the homozygous and heterozygous state. Support for the third cause of the disease comes from histopathological examinations of the temporal bones in patients with DFNA 9 (Ketharpal et al. (1991), *Arch. Otolaryngol. Head Neck Surg*. 117:1032–1042; Ketharpal (1993) *Arch. Otolaryngol. Head Neck Surg*. 119:106–108), that revealed the presence of acid mucopolysaccharide deposits in cochlear and vestibular nerve channels in the inner ear. These deposits lead to strangulation and degeneration of dendrites. A considerable loss of cochlear and vestibular neurons is observed, and the neurons that are left no longer have dendritic fibers. Since the COCHSB2 protein is probably a secreted and ligand-binding protein, it is tempting to speculate that one of novel deleterious properties may be or may lead to the formation of the insoluble deposits. Moreover, in situ hybridization of cochlea and vestibulum in chicken revealed that the COCH5B2 gene is expressed at the same sites where the mucopolysaccharide deposit is found, corroborating a primary role of COCH5B2 protein in the origin of the deposit and the pathogenesis of the disease. The fact that a homozygous patient has an earlier age of onset may reflect the fact that the deleterious protein is more abundant, and, consequently, a faster degeneration of cochlear and vestibular function may occur. This is consistent with the hypothesis that DFNA9 is caused by gain-of-function mutations, as it is possible that only very specific mutations enable the formation of the insoluble mucopolysaccharide deposit.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of identifying an individual at risk for Meniere disease, comprising:

providing an individual at risk for Meniere disease;

amplifying a nucleic acid sample from the individual which includes at least a portion of the gene encoding the polypeptide of SEQ ID NO:2, wherein the amplified portion of the gene includes residue 51 of SEQ ID NO:2, and detecting in the individual a genetic lesion in the gene that encodes a polypeptide comprising SEQ ID NO: 2, wherein the lesion is an insertion, a deletion, or a substitution of one or more nucleotides encoding the proline at residue 51 of SEQ ID NO:2, and wherein the presence of the lesion identifies an individual at risk for Meniere disease.

2. The method of claim 1, wherein the lesion is a deletion or substitution of a cytosine at nucleotide 151 of a COCH5B2 coding sequence of SEQ ID NO:1, or is an insertion at nucleotide 151 of a COCH5B2 coding sequence of SEQ ID NO:1.

3. The method of claim 1, wherein the lesion is a substitution.

4. The method of claim 3, wherein the substitution is of a cytosine at nucleotide 151 of a COCH5B2 coding sequence of SEQ ID NO:1.

5. The method of claim 1, further comprising contacting the amplified sample from the individual with an agent capable of detecting the genetic lesion in the gene.

6. The method of claim 5, wherein the agent is a nucleic acid probe.

7. The method of claim 6, wherein the probe is a labeled probe.

8. The method of claim 6, wherein the nucleic acid probe comprises at least 10 nucleotides from the nucleotide sequence of SEQ ID NO:4.

9. The method of claim 6, wherein the probe comprises the nucleic acid sequence of SEQ ID NO:6, or a portion thereof.

* * * * *

UNITED STATES PATENT AND TRADEMARK OFFICE

CERTIFICATE OF CORRECTION

PATENT NO. : 6,730,475 B1
DATED : May 4, 2004
INVENTOR(S) : Paul Van De Heyning et al.

It is certified that error appears in the above-identified patent and that said Letters Patent is hereby corrected as shown below:

Title page,
Item [56], References Cited, OTHER PUBLICATIONS, "Christiano et al. (1994)" reference, "20626" should be -- 20262 --; and "Halpin et al." reference, "1998" should be -- 1996 --.

Signed and Sealed this

Twenty-first Day of June, 2005

JON W. DUDAS
*Director of the United States Patent and Trademark Office*

UNITED STATES PATENT AND TRADEMARK OFFICE

CERTIFICATE OF CORRECTION

PATENT NO. : 6,730,475 B1
APPLICATION NO. : 09/579288
DATED : May 4, 2004
INVENTOR(S) : Paul Van De Heyning et al.

It is certified that error appears in the above-identified patent and that said Letters Patent is hereby corrected as shown below:

Col. 1, line 3;

After the title and before the background of the invention, please add the following paragraph:

STATEMENT AS TO FEDERALLY SPONSORED RESEARCH

This invention was made with Government support under Grant No. DC003402 awarded by the National Institutes of Health. The Government has certain rights in this invention.

Signed and Sealed this

Twenty-first Day of July, 2009

JOHN DOLL
*Acting Director of the United States Patent and Trademark Office*

SEQUENCE LISTING

```
<160> NUMBER OF SEQ ID NOS: 6

<210> SEQ ID NO 1
<211> LENGTH: 2534
<212> TYPE: DNA
<213> ORGANISM: Homo sapiens
<220> FEATURE:
<221> NAME/KEY: CDS
<222> LOCATION: (57)...(1706)

<400> SEQUENCE: 1

gcactcgggc gcagccgggt ggatctcgag caggtgtgag cagcctatca gtcacc atg      59
                                                              Met
                                                               1

tcc gca gcc tgg atc ccg gct ctc ggc ctc ggt gtg tgt ctg ctg ctg     107
Ser Ala Ala Trp Ile Pro Ala Leu Gly Leu Gly Val Cys Leu Leu Leu
            5                  10                  15

ctg ccg ggg ccc gcg ggc agc gag gga gcc gct ccc att gct atc aca     155
Leu Pro Gly Pro Ala Gly Ser Glu Gly Ala Ala Pro Ile Ala Ile Thr
        20                  25                  30

tgt ttt acc aga ggc ttg gac atc agg aaa gag aaa gca gat gtc ctc     203
Cys Phe Thr Arg Gly Leu Asp Ile Arg Lys Glu Lys Ala Asp Val Leu
    35                  40                  45

tgc cca ggg ggc tgc cct ctt gag gaa ttc tct gtg tat ggg aac ata     251
Cys Pro Gly Gly Cys Pro Leu Glu Glu Phe Ser Val Tyr Gly Asn Ile
 50                  55                  60                  65

gta tat gct tct gta tcg agc ata tgt ggg gct gct gtc cac agg gga     299
Val Tyr Ala Ser Val Ser Ser Ile Cys Gly Ala Ala Val His Arg Gly
                70                  75                  80

gta atc agc aac tca ggg gga cct gta cga gtc tat agc cta cct ggt     347
Val Ile Ser Asn Ser Gly Gly Pro Val Arg Val Tyr Ser Leu Pro Gly
            85                  90                  95

cga gaa aac tat tcc tca gta gat gcc aat ggc atc cag tct caa atg     395
Arg Glu Asn Tyr Ser Ser Val Asp Ala Asn Gly Ile Gln Ser Gln Met
        100                 105                 110

ctt tct aga tgg tct gct tct ttc aca gta act aaa ggc aaa agt agt     443
Leu Ser Arg Trp Ser Ala Ser Phe Thr Val Thr Lys Gly Lys Ser Ser
    115                 120                 125

aca cag gag gcc aca gga caa gca gtg tcc aca gca cat cca cca aca     491
Thr Gln Glu Ala Thr Gly Gln Ala Val Ser Thr Ala His Pro Pro Thr
130                 135                 140                 145

ggt aaa cga cta aag aaa aca ccc gag aag aaa act ggc aat aaa gat     539
Gly Lys Arg Leu Lys Lys Thr Pro Glu Lys Lys Thr Gly Asn Lys Asp
                150                 155                 160

tgt aaa gca gac att gca ttt ctg att gat gga agc ttt aat att ggg     587
Cys Lys Ala Asp Ile Ala Phe Leu Ile Asp Gly Ser Phe Asn Ile Gly
            165                 170                 175

cag cgc cga ttt aat tta cag aag aat ttt gtt gga aaa gtg gct cta     635
Gln Arg Arg Phe Asn Leu Gln Lys Asn Phe Val Gly Lys Val Ala Leu
        180                 185                 190

atg ttg gga att gga aca gaa gga cca cat gtg ggc ctt gtt caa gcc     683
Met Leu Gly Ile Gly Thr Glu Gly Pro His Val Gly Leu Val Gln Ala
    195                 200                 205

agt gaa cat ccc aaa ata gaa ttt tac ttg aaa aac ttt aca tca gcc     731
Ser Glu His Pro Lys Ile Glu Phe Tyr Leu Lys Asn Phe Thr Ser Ala
210                 215                 220                 225

aaa gat gtt ttg ttt gcc ata aag gaa gta ggt ttc aga ggg ggt aat     779
Lys Asp Val Leu Phe Ala Ile Lys Glu Val Gly Phe Arg Gly Gly Asn
                230                 235                 240
```

-continued

```
tcc aat aca gga aaa gcc ttg aag cat act gct cag aaa ttc ttc acg      827
Ser Asn Thr Gly Lys Ala Leu Lys His Thr Ala Gln Lys Phe Phe Thr
            245                 250                 255

gta gat gct gga gta aga aaa ggg atc ccc aaa gtg gtg gtg gta ttt      875
Val Asp Ala Gly Val Arg Lys Gly Ile Pro Lys Val Val Val Val Phe
        260                 265                 270

att gat ggt tgg cct tct gat gac atc gag gaa gca ggc att gtg gcc      923
Ile Asp Gly Trp Pro Ser Asp Asp Ile Glu Glu Ala Gly Ile Val Ala
    275                 280                 285

aga gag ttt ggt gtc aat gta ttt ata gtt tct gtg gcc aag cct atc      971
Arg Glu Phe Gly Val Asn Val Phe Ile Val Ser Val Ala Lys Pro Ile
290                 295                 300                 305

cct gaa gaa ctg ggg atg gtt cag gat gtc aca ttt gtt gac aag gct     1019
Pro Glu Glu Leu Gly Met Val Gln Asp Val Thr Phe Val Asp Lys Ala
                310                 315                 320

gtc tgt cgg aat aat ggc ttc ttc tct tac cac atg ccc aac tgg ttt     1067
Val Cys Arg Asn Asn Gly Phe Phe Ser Tyr His Met Pro Asn Trp Phe
            325                 330                 335

ggc acc aca aaa tac gta aag cct ctg gta cag aag ctg tgc act cat     1115
Gly Thr Thr Lys Tyr Val Lys Pro Leu Val Gln Lys Leu Cys Thr His
        340                 345                 350

gaa caa atg atg tgc agc aag acc tgt tat aac tca gtg aac att gcc     1163
Glu Gln Met Met Cys Ser Lys Thr Cys Tyr Asn Ser Val Asn Ile Ala
    355                 360                 365

ttt cta att gat ggc tcc agc agt gtt gga gat agc aat ttc cgc ctc     1211
Phe Leu Ile Asp Gly Ser Ser Ser Val Gly Asp Ser Asn Phe Arg Leu
370                 375                 380                 385

atg ctt gaa ttt gtt tcc aac ata gcc aag act ttt gaa atc tcg gac     1259
Met Leu Glu Phe Val Ser Asn Ile Ala Lys Thr Phe Glu Ile Ser Asp
                390                 395                 400

att ggt gcc aag ata gct gct gta cag ttt act tat gat cag cgc acg     1307
Ile Gly Ala Lys Ile Ala Ala Val Gln Phe Thr Tyr Asp Gln Arg Thr
            405                 410                 415

gag ttc agt ttc act gac tat agc acc aaa gag aat gtc cta gct gtc     1355
Glu Phe Ser Phe Thr Asp Tyr Ser Thr Lys Glu Asn Val Leu Ala Val
        420                 425                 430

atc aga aac atc cgc tat atg agt ggt gga aca gct act ggt gat gcc     1403
Ile Arg Asn Ile Arg Tyr Met Ser Gly Gly Thr Ala Thr Gly Asp Ala
    435                 440                 445

att tcc ttc act gtt aga aat gtg ttt ggc cct ata agg gag agc ccc     1451
Ile Ser Phe Thr Val Arg Asn Val Phe Gly Pro Ile Arg Glu Ser Pro
450                 455                 460                 465

aac aag aac ttc cta gta att gtc aca gat ggg cag tcc tat gat gat     1499
Asn Lys Asn Phe Leu Val Ile Val Thr Asp Gly Gln Ser Tyr Asp Asp
                470                 475                 480

gtc caa ggc cct gca gct gct gca cat gat gca gga atc act atc ttc     1547
Val Gln Gly Pro Ala Ala Ala Ala His Asp Ala Gly Ile Thr Ile Phe
            485                 490                 495

tct gtt ggt gtg gct tgg gca cct ctg gat gac ctg aaa gat atg gct     1595
Ser Val Gly Val Ala Trp Ala Pro Leu Asp Asp Leu Lys Asp Met Ala
        500                 505                 510

tct aaa ccg aag gag tct cat gct ttc ttc aca aga gag ttc aca gga     1643
Ser Lys Pro Lys Glu Ser His Ala Phe Phe Thr Arg Glu Phe Thr Gly
    515                 520                 525

tta gaa cca att gtt tct gat gtc atc aga ggc att tgt aga gat ttc     1691
Leu Glu Pro Ile Val Ser Asp Val Ile Arg Gly Ile Cys Arg Asp Phe
530                 535                 540                 545

tta gaa tcc cag caa taatggtaac attttgacaa ctgaaagaaa aagtacaagg     1746
Leu Glu Ser Gln Gln
                550
```

```
ggatccagtg tgtaaattgt attctcataa tactgaaatg ctttagcata ctagaatcag   1806

atacaaaact attaagtatg tcaacagcca tttaggcaaa taagcactcc tttaaagccg   1866

ctgccttctg gttacaattt acagtgtact ttgttaaaaa cactgctgag gcttcataat   1926

catggctctt agaaactcag gaaagaggag ataatgtgga ttaaaacctt aagagttcta   1986

accatgccta ctaaatgtac agatatgcaa attccatagc tcaataaaag aatctgatac   2046

ttagaccaaa agcaacattc gttctctaac cattctgtat tgattatata agcaaaatga   2106

aaagagaaac ttaaatgaac acagctcttt aacatggttc aggtacacat attttgaccc   2166

aagtggatat tttcttaaaa ccaatcaata atagctagct attactgcag actataaaat   2226

ctggatatag aaaggagacc tgtatcaaac tgcttttgta gtgtgttttc ataacaactt   2286

atgactaaaa atatcacact gaataagaga gcaggattgc caggtatttt tctatttctc   2346

tccttaattt tatatgtata tagatatatt tggcttatat tctaagtcac ctaagtactt   2406

aaaagttaag ttggtaaagt atttactgac tgcttataaa catttaaaga caaagacatt   2466

tcaaataact gcagaaaaaa tattgtagtt tgaatattta agcaataaaa ctgctagtga   2526

gttattgt                                                            2534
```

```
<210> SEQ ID NO 2
<211> LENGTH: 550
<212> TYPE: PRT
<213> ORGANISM: Homo sapiens

<400> SEQUENCE: 2

Met Ser Ala Ala Trp Ile Pro Ala Leu Gly Leu Gly Val Cys Leu Leu
 1               5                  10                  15

Leu Leu Pro Gly Pro Ala Gly Ser Glu Gly Ala Ala Pro Ile Ala Ile
            20                  25                  30

Thr Cys Phe Thr Arg Gly Leu Asp Ile Arg Lys Glu Lys Ala Asp Val
        35                  40                  45

Leu Cys Pro Gly Gly Cys Pro Leu Glu Glu Phe Ser Val Tyr Gly Asn
    50                  55                  60

Ile Val Tyr Ala Ser Val Ser Ser Ile Cys Gly Ala Ala Val His Arg
65                  70                  75                  80

Gly Val Ile Ser Asn Ser Gly Gly Pro Val Arg Val Tyr Ser Leu Pro
                85                  90                  95

Gly Arg Glu Asn Tyr Ser Ser Val Asp Ala Asn Gly Ile Gln Ser Gln
            100                 105                 110

Met Leu Ser Arg Trp Ser Ala Ser Phe Thr Val Thr Lys Gly Lys Ser
        115                 120                 125

Ser Thr Gln Glu Ala Thr Gly Gln Ala Val Ser Thr Ala His Pro Pro
    130                 135                 140

Thr Gly Lys Arg Leu Lys Lys Thr Pro Glu Lys Lys Thr Gly Asn Lys
145                 150                 155                 160

Asp Cys Lys Ala Asp Ile Ala Phe Leu Ile Asp Gly Ser Phe Asn Ile
                165                 170                 175

Gly Gln Arg Arg Phe Asn Leu Gln Lys Asn Phe Val Gly Lys Val Ala
            180                 185                 190

Leu Met Leu Gly Ile Gly Thr Glu Gly Pro His Val Gly Leu Val Gln
        195                 200                 205

Ala Ser Glu His Pro Lys Ile Glu Phe Tyr Leu Lys Asn Phe Thr Ser
    210                 215                 220
```

-continued

```
Ala Lys Asp Val Leu Phe Ala Ile Lys Glu Val Gly Phe Arg Gly Gly
225                 230                 235                 240

Asn Ser Asn Thr Gly Lys Ala Leu Lys His Thr Ala Gln Lys Phe Phe
                245                 250                 255

Thr Val Asp Ala Gly Val Arg Lys Gly Ile Pro Lys Val Val Val Val
            260                 265                 270

Phe Ile Asp Gly Trp Pro Ser Asp Asp Ile Glu Glu Ala Gly Ile Val
        275                 280                 285

Ala Arg Glu Phe Gly Val Asn Val Phe Ile Val Ser Val Ala Lys Pro
    290                 295                 300

Ile Pro Glu Glu Leu Gly Met Val Gln Asp Val Thr Phe Val Asp Lys
305                 310                 315                 320

Ala Val Cys Arg Asn Asn Gly Phe Phe Ser Tyr His Met Pro Asn Trp
                325                 330                 335

Phe Gly Thr Thr Lys Tyr Val Lys Pro Leu Val Gln Lys Leu Cys Thr
            340                 345                 350

His Glu Gln Met Met Cys Ser Lys Thr Cys Tyr Asn Ser Val Asn Ile
        355                 360                 365

Ala Phe Leu Ile Asp Gly Ser Ser Ser Val Gly Asp Ser Asn Phe Arg
    370                 375                 380

Leu Met Leu Glu Phe Val Ser Asn Ile Ala Lys Thr Phe Glu Ile Ser
385                 390                 395                 400

Asp Ile Gly Ala Lys Ile Ala Ala Val Gln Phe Thr Tyr Asp Gln Arg
                405                 410                 415

Thr Glu Phe Ser Phe Thr Asp Tyr Ser Thr Lys Glu Asn Val Leu Ala
            420                 425                 430

Val Ile Arg Asn Ile Arg Tyr Met Ser Gly Gly Thr Ala Thr Gly Asp
        435                 440                 445

Ala Ile Ser Phe Thr Val Arg Asn Val Phe Gly Pro Ile Arg Glu Ser
    450                 455                 460

Pro Asn Lys Asn Phe Leu Val Ile Val Thr Asp Gly Gln Ser Tyr Asp
465                 470                 475                 480

Asp Val Gln Gly Pro Ala Ala Ala Ala His Asp Ala Gly Ile Thr Ile
                485                 490                 495

Phe Ser Val Gly Val Ala Trp Ala Pro Leu Asp Asp Leu Lys Asp Met
            500                 505                 510

Ala Ser Lys Pro Lys Glu Ser His Ala Phe Phe Thr Arg Glu Phe Thr
        515                 520                 525

Gly Leu Glu Pro Ile Val Ser Asp Val Ile Arg Gly Ile Cys Arg Asp
    530                 535                 540

Phe Leu Glu Ser Gln Gln
545                 550
```

<210> SEQ ID NO 3
<211> LENGTH: 1650
<212> TYPE: DNA
<213> ORGANISM: Homo sapiens

<400> SEQUENCE: 3

```
atgtccgcag cctggatccc ggctctcggc ctcggtgtgt gtctgctgct gctgccgggg      60

cccgcgggca gcgagggagc cgctcccatt gctatcacat gttttaccag aggcttggac     120

atcaggaaag agaaagcaga tgtcctctgc ccaggggggct gccctcttga ggaattctct     180

gtgtatggga acatagtata tgcttctgta tcgagcatat gtggggctgc tgtccacagg     240
```

-continued

```
ggagtaatca gcaactcagg gggacctgta cgagtctata gcctacctgg tcgagaaaac    300

tattcctcag tagatgccaa tggcatccag tctcaaatgc tttctagatg gtctgcttct    360

ttcacagtaa ctaaaggcaa aagtagtaca caggaggcca caggacaagc agtgtccaca    420

gcacatccac caacaggtaa acgactaaag aaaacacccg agaagaaaac tggcaataaa    480

gattgtaaag cagacattgc atttctgatt gatggaagct ttaatattgg gcagcgccga    540

tttaatttac agaagaattt tgttggaaaa gtggctctaa tgttgggaat tggaacagaa    600

ggaccacatg tgggccttgt tcaagccagt gaacatccca aaatagaatt ttacttgaaa    660

aactttacat cagccaaaga tgttttgttt gccataaagg aagtaggttt cagagggggt    720

aattccaata caggaaaagc cttgaagcat actgctcaga aattcttcac ggtagatgct    780

ggagtaagaa aagggatccc caaagtggtg gtggtattta ttgatggttg gccttctgat    840

gacatcgagg aagcaggcat tgtggccaga gagtttggtg tcaatgtatt tatagtttct    900

gtggccaagc ctatccctga agaactgggg atggttcagg atgtcacatt tgttgacaag    960

gctgtctgtc ggaataatgg cttcttctct taccacatgc ccaactggtt tggcaccaca   1020

aaatacgtaa agcctctggt acagaagctg tgcactcatg aacaaatgat gtgcagcaag   1080

acctgttata actcagtgaa cattgccttt ctaattgatg gctccagcag tgttggagat   1140

agcaatttcc gcctcatgct tgaatttgtt tccaacatag ccaagacttt tgaaatctcg   1200

gacattggtg ccaagatagc tgctgtacag tttacttatg atcagcgcac ggagttcagt   1260

ttcactgact atagcaccaa agagaatgtc ctagctgtca tcagaaacat ccgctatatg   1320

agtggtggaa cagctactgg tgatgccatt tccttcactg ttagaaatgt gtttggccct   1380

ataagggaga gccccaacaa gaacttccta gtaattgtca cagatgggca gtcctatgat   1440

gatgtccaag gccctgcagc tgctgcacat gatgcaggaa tcactatctt ctctgttggt   1500

gtggcttggg cacctctgga tgacctgaaa gatatggctt ctaaaccgaa ggagtctcat   1560

gctttcttca caagagagtt cacaggatta gaaccaattg tttctgatgt catcagaggc   1620

atttgtagag atttcttaga atcccagcaa                                    1650
```

```
<210> SEQ ID NO 4
<211> LENGTH: 2534
<212> TYPE: DNA
<213> ORGANISM: Homo sapiens
<220> FEATURE:
<221> NAME/KEY: CDS
<222> LOCATION: (57)...(1706)

<400> SEQUENCE: 4

gcactcgggc gcagccgggt ggatctcgag caggtgtgag cagcctatca gtcacc atg     59
                                                              Met
                                                               1

tcc gca gcc tgg atc ccg gct ctc ggc ctc ggt gtg tgt ctg ctg ctg      107
Ser Ala Ala Trp Ile Pro Ala Leu Gly Leu Gly Val Cys Leu Leu Leu
            5                  10                  15

ctg ccg ggg ccc gcg ggc agc gag gga gcc gct ccc att gct atc aca      155
Leu Pro Gly Pro Ala Gly Ser Glu Gly Ala Ala Pro Ile Ala Ile Thr
        20                  25                  30

tgt ttt acc aga ggc ttg gac atc agg aaa gag aaa gca gat gtc ctc      203
Cys Phe Thr Arg Gly Leu Asp Ile Arg Lys Glu Lys Ala Asp Val Leu
    35                  40                  45

tgc tca ggg ggc tgc cct ctt gag gaa ttc tct gtg tat ggg aac ata      251
Cys Ser Gly Gly Cys Pro Leu Glu Glu Phe Ser Val Tyr Gly Asn Ile
 50                  55                  60                  65
```

-continued

```
gta tat gct tct gta tcg agc ata tgt ggg gct gct gtc cac agg gga      299
Val Tyr Ala Ser Val Ser Ser Ile Cys Gly Ala Ala Val His Arg Gly
                 70                  75                  80

gta atc agc aac tca ggg gga cct gta cga gtc tat agc cta cct ggt      347
Val Ile Ser Asn Ser Gly Gly Pro Val Arg Val Tyr Ser Leu Pro Gly
             85                  90                  95

cga gaa aac tat tcc tca gta gat gcc aat ggc atc cag tct caa atg      395
Arg Glu Asn Tyr Ser Ser Val Asp Ala Asn Gly Ile Gln Ser Gln Met
        100                 105                 110

ctt tct aga tgg tct gct tct ttc aca gta act aaa ggc aaa agt agt      443
Leu Ser Arg Trp Ser Ala Ser Phe Thr Val Thr Lys Gly Lys Ser Ser
    115                 120                 125

aca cag gag gcc aca gga caa gca gtg tcc aca gca cat cca cca aca      491
Thr Gln Glu Ala Thr Gly Gln Ala Val Ser Thr Ala His Pro Pro Thr
130                 135                 140                 145

ggt aaa cga cta aag aaa aca ccc gag aag aaa act ggc aat aaa gat      539
Gly Lys Arg Leu Lys Lys Thr Pro Glu Lys Lys Thr Gly Asn Lys Asp
                150                 155                 160

tgt aaa gca gac att gca ttt ctg att gat gga agc ttt aat att ggg      587
Cys Lys Ala Asp Ile Ala Phe Leu Ile Asp Gly Ser Phe Asn Ile Gly
            165                 170                 175

cag cgc cga ttt aat tta cag aag aat ttt gtt gga aaa gtg gct cta      635
Gln Arg Arg Phe Asn Leu Gln Lys Asn Phe Val Gly Lys Val Ala Leu
        180                 185                 190

atg ttg gga att gga aca gaa gga cca cat gtg ggc ctt gtt caa gcc      683
Met Leu Gly Ile Gly Thr Glu Gly Pro His Val Gly Leu Val Gln Ala
    195                 200                 205

agt gaa cat ccc aaa ata gaa ttt tac ttg aaa aac ttt aca tca gcc      731
Ser Glu His Pro Lys Ile Glu Phe Tyr Leu Lys Asn Phe Thr Ser Ala
210                 215                 220                 225

aaa gat gtt ttg ttt gcc ata aag gaa gta ggt ttc aga ggg ggt aat      779
Lys Asp Val Leu Phe Ala Ile Lys Glu Val Gly Phe Arg Gly Gly Asn
                230                 235                 240

tcc aat aca gga aaa gcc ttg aag cat act gct cag aaa ttc ttc acg      827
Ser Asn Thr Gly Lys Ala Leu Lys His Thr Ala Gln Lys Phe Phe Thr
            245                 250                 255

gta gat gct gga gta aga aaa ggg atc ccc aaa gtg gtg gtg gta ttt      875
Val Asp Ala Gly Val Arg Lys Gly Ile Pro Lys Val Val Val Val Phe
        260                 265                 270

att gat ggt tgg cct tct gat gac atc gag gaa gca ggc att gtg gcc      923
Ile Asp Gly Trp Pro Ser Asp Asp Ile Glu Glu Ala Gly Ile Val Ala
    275                 280                 285

aga gag ttt ggt gtc aat gta ttt ata gtt tct gtg gcc aag cct atc      971
Arg Glu Phe Gly Val Asn Val Phe Ile Val Ser Val Ala Lys Pro Ile
290                 295                 300                 305

cct gaa gaa ctg ggg atg gtt cag gat gtc aca ttt gtt gac aag gct     1019
Pro Glu Glu Leu Gly Met Val Gln Asp Val Thr Phe Val Asp Lys Ala
                310                 315                 320

gtc tgt cgg aat aat ggc ttc ttc tct tac cac atg ccc aac tgg ttt     1067
Val Cys Arg Asn Asn Gly Phe Phe Ser Tyr His Met Pro Asn Trp Phe
            325                 330                 335

ggc acc aca aaa tac gta aag cct ctg gta cag aag ctg tgc act cat     1115
Gly Thr Thr Lys Tyr Val Lys Pro Leu Val Gln Lys Leu Cys Thr His
        340                 345                 350

gaa caa atg atg tgc agc aag acc tgt tat aac tca gtg aac att gcc     1163
Glu Gln Met Met Cys Ser Lys Thr Cys Tyr Asn Ser Val Asn Ile Ala
    355                 360                 365

ttt cta att gat ggc tcc agc agt gtt gga gat agc aat ttc cgc ctc     1211
Phe Leu Ile Asp Gly Ser Ser Ser Val Gly Asp Ser Asn Phe Arg Leu
370                 375                 380                 385
```

-continued

```
atg ctt gaa ttt gtt tcc aac ata gcc aag act ttt gaa atc tcg gac     1259
Met Leu Glu Phe Val Ser Asn Ile Ala Lys Thr Phe Glu Ile Ser Asp
                390                 395                 400

att ggt gcc aag ata gct gct gta cag ttt act tat gat cag cgc acg     1307
Ile Gly Ala Lys Ile Ala Ala Val Gln Phe Thr Tyr Asp Gln Arg Thr
            405                 410                 415

gag ttc agt ttc act gac tat agc acc aaa gag aat gtc cta gct gtc     1355
Glu Phe Ser Phe Thr Asp Tyr Ser Thr Lys Glu Asn Val Leu Ala Val
        420                 425                 430

atc aga aac atc cgc tat atg agt ggt gga aca gct act ggt gat gcc     1403
Ile Arg Asn Ile Arg Tyr Met Ser Gly Gly Thr Ala Thr Gly Asp Ala
    435                 440                 445

att tcc ttc act gtt aga aat gtg ttt ggc cct ata agg gag agc ccc     1451
Ile Ser Phe Thr Val Arg Asn Val Phe Gly Pro Ile Arg Glu Ser Pro
450                 455                 460                 465

aac aag aac ttc cta gta att gtc aca gat ggg cag tcc tat gat gat     1499
Asn Lys Asn Phe Leu Val Ile Val Thr Asp Gly Gln Ser Tyr Asp Asp
                470                 475                 480

gtc caa ggc cct gca gct gct gca cat gat gca gga atc act atc ttc     1547
Val Gln Gly Pro Ala Ala Ala Ala His Asp Ala Gly Ile Thr Ile Phe
            485                 490                 495

tct gtt ggt gtg gct tgg gca cct ctg gat gac ctg aaa gat atg gct     1595
Ser Val Gly Val Ala Trp Ala Pro Leu Asp Asp Leu Lys Asp Met Ala
        500                 505                 510

tct aaa ccg aag gag tct cat gct ttc ttc aca aga gag ttc aca gga     1643
Ser Lys Pro Lys Glu Ser His Ala Phe Phe Thr Arg Glu Phe Thr Gly
    515                 520                 525

tta gaa cca att gtt tct gat gtc atc aga ggc att tgt aga gat ttc     1691
Leu Glu Pro Ile Val Ser Asp Val Ile Arg Gly Ile Cys Arg Asp Phe
530                 535                 540                 545

tta gaa tcc cag caa taatggtaac attttgacaa ctgaaagaaa aagtacaagg     1746
Leu Glu Ser Gln Gln
                550

ggatccagtg tgtaaattgt attctcataa tactgaaatg ctttagcata ctagaatcag   1806

atacaaaact attaagtatg tcaacagcca tttaggcaaa taagcactcc tttaaagccg   1866

ctgccttctg gttacaattt acagtgtact ttgttaaaaa cactgctgag gcttcataat   1926

catggctctt agaaactcag gaaagaggag ataatgtgga ttaaaacctt aagagttcta   1986

accatgccta ctaaatgtac agatatgcaa attccatagc tcaataaaag aatctgatac   2046

ttagaccaaa agcaacattc gttctctaac cattctgtat tgattatata agcaaaatga   2106

aaagagaaac ttaaatgaac acagctcttt aacatggttc aggtacacat attttgaccc   2166

aagtggatat tttcttaaaa ccaatcaata atagctagct attactgcag actataaaat   2226

ctggatatag aaaggagacc tgtatcaaac tgcttttgta gtgtgttttc ataacaactt   2286

atgactaaaa atatcacact gaataagaga gcaggattgc caggtatttt tctatttctc   2346

tccttaattt tatatgtata tagatatatt tggcttatat tctaagtcac ctaagtactt   2406

aaaagttaag ttggtaaagt atttactgac tgcttataaa catttaaaga caaagacatt   2466

tcaaataact gcagaaaaaa tattgtagtt tgaatattta agcaataaaa ctgctagtga   2526

gttattgt                                                             2534
```

<210> SEQ ID NO 5
<211> LENGTH: 550
<212> TYPE: PRT
<213> ORGANISM: Homo sapiens -continued

<400> SEQUENCE: 5

```
Met Ser Ala Ala Trp Ile Pro Ala Leu Gly Leu Gly Val Cys Leu Leu
 1               5                  10                  15

Leu Leu Pro Gly Pro Ala Gly Ser Glu Gly Ala Ala Pro Ile Ala Ile
            20                  25                  30

Thr Cys Phe Thr Arg Gly Leu Asp Ile Arg Lys Glu Lys Ala Asp Val
        35                  40                  45

Leu Cys Ser Gly Gly Cys Pro Leu Glu Glu Phe Ser Val Tyr Gly Asn
    50                  55                  60

Ile Val Tyr Ala Ser Val Ser Ser Ile Cys Gly Ala Ala Val His Arg
65                  70                  75                  80

Gly Val Ile Ser Asn Ser Gly Gly Pro Val Arg Val Tyr Ser Leu Pro
                85                  90                  95

Gly Arg Glu Asn Tyr Ser Ser Val Asp Ala Asn Gly Ile Gln Ser Gln
            100                 105                 110

Met Leu Ser Arg Trp Ser Ala Ser Phe Thr Val Thr Lys Gly Lys Ser
        115                 120                 125

Ser Thr Gln Glu Ala Thr Gly Gln Ala Val Ser Thr Ala His Pro Pro
    130                 135                 140

Thr Gly Lys Arg Leu Lys Lys Thr Pro Glu Lys Lys Thr Gly Asn Lys
145                 150                 155                 160

Asp Cys Lys Ala Asp Ile Ala Phe Leu Ile Asp Gly Ser Phe Asn Ile
                165                 170                 175

Gly Gln Arg Arg Phe Asn Leu Gln Lys Asn Phe Val Gly Lys Val Ala
            180                 185                 190

Leu Met Leu Gly Ile Gly Thr Glu Gly Pro His Val Gly Leu Val Gln
        195                 200                 205

Ala Ser Glu His Pro Lys Ile Glu Phe Tyr Leu Lys Asn Phe Thr Ser
    210                 215                 220

Ala Lys Asp Val Leu Phe Ala Ile Lys Glu Val Gly Phe Arg Gly Gly
225                 230                 235                 240

Asn Ser Asn Thr Gly Lys Ala Leu Lys His Thr Ala Gln Lys Phe Phe
                245                 250                 255

Thr Val Asp Ala Gly Val Arg Lys Gly Ile Pro Lys Val Val Val Val
            260                 265                 270

Phe Ile Asp Gly Trp Pro Ser Asp Asp Ile Glu Glu Ala Gly Ile Val
        275                 280                 285

Ala Arg Glu Phe Gly Val Asn Val Phe Ile Val Ser Val Ala Lys Pro
    290                 295                 300

Ile Pro Glu Glu Leu Gly Met Val Gln Asp Val Thr Phe Val Asp Lys
305                 310                 315                 320

Ala Val Cys Arg Asn Asn Gly Phe Phe Ser Tyr His Met Pro Asn Trp
                325                 330                 335

Phe Gly Thr Thr Lys Tyr Val Lys Pro Leu Val Gln Lys Leu Cys Thr
            340                 345                 350

His Glu Gln Met Met Cys Ser Lys Thr Cys Tyr Asn Ser Val Asn Ile
        355                 360                 365

Ala Phe Leu Ile Asp Gly Ser Ser Ser Val Gly Asp Ser Asn Phe Arg
    370                 375                 380

Leu Met Leu Glu Phe Val Ser Asn Ile Ala Lys Thr Phe Glu Ile Ser
385                 390                 395                 400

Asp Ile Gly Ala Lys Ile Ala Ala Val Gln Phe Thr Tyr Asp Gln Arg
                405                 410                 415
```

-continued

```
Thr Glu Phe Ser Phe Thr Asp Tyr Ser Thr Lys Glu Asn Val Leu Ala
            420                 425                 430

Val Ile Arg Asn Ile Arg Tyr Met Ser Gly Gly Thr Ala Thr Gly Asp
        435                 440                 445

Ala Ile Ser Phe Thr Val Arg Asn Val Phe Gly Pro Ile Arg Glu Ser
    450                 455                 460

Pro Asn Lys Asn Phe Leu Val Ile Val Thr Asp Gly Gln Ser Tyr Asp
465                 470                 475                 480

Asp Val Gln Gly Pro Ala Ala Ala Ala His Asp Ala Gly Ile Thr Ile
                485                 490                 495

Phe Ser Val Gly Val Ala Trp Ala Pro Leu Asp Asp Leu Lys Asp Met
            500                 505                 510

Ala Ser Lys Pro Lys Glu Ser His Ala Phe Phe Thr Arg Glu Phe Thr
        515                 520                 525

Gly Leu Glu Pro Ile Val Ser Asp Val Ile Arg Gly Ile Cys Arg Asp
    530                 535                 540

Phe Leu Glu Ser Gln Gln
545                 550

<210> SEQ ID NO 6
<211> LENGTH: 17
<212> TYPE: DNA
<213> ORGANISM: Artificial Sequence
<220> FEATURE:
<223> OTHER INFORMATION: synthetically generated probe

<400> SEQUENCE: 6

tcctctgctc agggggc                                                  17
```